(12) United States Patent
Payton et al.

(10) Patent No.: US 10,973,466 B2
(45) Date of Patent: Apr. 13, 2021

(54) SYSTEM FOR DETERMINING AIRWAY PATENCY

(71) Applicant: Fisher & Paykel Healthcare Limited, Auckland (NZ)

(72) Inventors: Matthew Jon Payton, Auckland (NZ); Alireza Nejati Javaremi, Auckland (NZ); Thomas Heinrich Barnes, Surrey (GB); Laith Adeeb Hermez, Auckland (NZ); Rachael Glaves, Auckland (NZ); Samantha Dale Oldfield, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 289 days.

(21) Appl. No.: 16/096,640

(22) PCT Filed: Apr. 28, 2017

(86) PCT No.: PCT/IB2017/052458
§ 371 (c)(1),
(2) Date: Oct. 25, 2018

(87) PCT Pub. No.: WO2017/187391
PCT Pub. Date: Nov. 2, 2017

(65) Prior Publication Data
US 2019/0150831 A1    May 23, 2019

Related U.S. Application Data

(60) Provisional application No. 62/329,555, filed on Apr. 29, 2016.

(51) Int. Cl.
*A61B 5/08* (2006.01)
*A61M 16/16* (2006.01)
(Continued)

(52) U.S. Cl.
CPC ............. *A61B 5/7246* (2013.01); *A61B 5/082* (2013.01); *A61B 5/083* (2013.01); *A61B 5/087* (2013.01);
(Continued)

(58) Field of Classification Search
CPC ..... A61B 5/0205; A61B 5/0813; A61B 5/082; A61B 5/083; A61B 5/0836; A61B 5/087;
(Continued)

(56) References Cited

U.S. PATENT DOCUMENTS 6,675,797 B1 * 1/2004 Berthon-Jones ....... A61B 5/087
128/204.18
6,739,335 B1    5/2004 Rapport et al.
(Continued)

FOREIGN PATENT DOCUMENTS

WO    WO 2005/079897    9/2005
WO    WO 2015/110374    7/2015
(Continued)

OTHER PUBLICATIONS

Aug. 14, 2017, PCT International Search Report for Application No. PCT/IB2017/052458.
(Continued)

*Primary Examiner* — Joseph D. Boecker
(74) *Attorney, Agent, or Firm* — Knobbe Martens Olson and Bear, LLP

(57) ABSTRACT

This invention relates to a method or system for providing an indication or establishment of airway patency of a patient comprising monitoring of at least one targeted gas (e.g. CO2, N2 or may be other gases capable of being detected, monitored, and measured) that is being expired or being expelled from an airway of a patient (e.g. an apnoeic or non-spontaneously breathing patient), and based on measurements of the at least one targeted gas for a period of
(Continued)

time, providing an indicator as to an output of the measurements of the at least one targeted gas for the period of time, or a determination as to airway patency, or a determination as to a location of a blockage or obstruction in the airway, or combinations of these.

19 Claims, 14 Drawing Sheets

(51) Int. Cl.
| | |
|---|---|
| *A61M 16/00* | (2006.01) |
| *A61M 16/10* | (2006.01) |
| *A61B 5/097* | (2006.01) |
| *A61B 5/083* | (2006.01) |
| *A61B 5/087* | (2006.01) |
| *A61M 16/06* | (2006.01) |
| *A61M 16/12* | (2006.01) |
| *A61B 5/00* | (2006.01) |
| *A61B 5/0205* | (2006.01) |
| *A61B 5/024* | (2006.01) |
| *A61B 5/091* | (2006.01) |
| *A61B 5/1455* | (2006.01) |
| *A61B 5/085* | (2006.01) |

(52) U.S. Cl.
CPC ............ *A61B 5/097* (2013.01); *A61B 5/4836* (2013.01); *A61B 5/682* (2013.01); *A61M 16/0006* (2014.02); *A61M 16/024* (2017.08); *A61M 16/0616* (2014.02); *A61M 16/0666* (2013.01); *A61M 16/1005* (2014.02); *A61M 16/107* (2014.02); *A61M 16/12* (2013.01); *A61M 16/16* (2013.01); *A61B 5/024* (2013.01); *A61B 5/0205* (2013.01); *A61B 5/02416* (2013.01); *A61B 5/085* (2013.01); *A61B 5/0813* (2013.01); *A61B 5/0833* (2013.01); *A61B 5/0836* (2013.01); *A61B 5/091* (2013.01); *A61B 5/14551* (2013.01); *A61B 2562/0247* (2013.01); *A61M 2016/003* (2013.01); *A61M 2016/0033* (2013.01); *A61M 2016/103* (2013.01); *A61M 2016/1025* (2013.01); *A61M 2016/1035* (2013.01); *A61M 2202/025* (2013.01); *A61M 2205/18* (2013.01); *A61M 2205/581* (2013.01); *A61M 2205/582* (2013.01); *A61M 2205/583* (2013.01)

(58) Field of Classification Search
CPC ....... A61B 5/091; A61B 5/097; A61B 5/7246; A61M 2016/0027; A61M 2016/003; A61M 2016/0033; A61M 2016/0413; A61M 2016/1025; A61M 2016/103; A61M 2016/1035; A61M 2230/04; A61M 2230/06; A61M 2230/43; A61M 2230/432; A61M 2230/435; A61M 2230/437; A61M 16/00; A61M 16/0003; A61M 16/0006; A61M 16/0051; A61M 16/0057; A61M 16/0066; A61M 16/0069; A61M 16/0078; A61M 16/0084; A61M 16/01; A61M 16/022; A61M 16/024; A61M 16/04; A61M 16/06; A61M 16/0666; A61M 16/0841; A61M 16/085; A61M 16/1005; A61M 16/12; A61M 16/16

See application file for complete search history.

(56) References Cited

U.S. PATENT DOCUMENTS

| | | | |
|---|---|---|---|
| 2002/0017300 A1* | 2/2002 | Hickle | A61B 5/0836 128/204.22 |
| 2004/0230108 A1* | 11/2004 | Melker | A61B 5/6829 600/340 |
| 2008/0300500 A1* | 12/2008 | Reisfeld | A61B 5/0402 600/532 |
| 2010/0170507 A1 | 7/2010 | Tanaka et al. | |
| 2010/0174161 A1* | 7/2010 | Lynn | A61B 5/002 600/323 |
| 2011/0180064 A1 | 7/2011 | Tanaka et al. | |
| 2015/0190088 A1* | 7/2015 | Chen | A61B 5/02055 600/301 |
| 2015/0306325 A1* | 10/2015 | Lapoint | A61M 16/024 128/204.23 |
| 2016/0045154 A1* | 2/2016 | Addison | A61B 5/082 600/301 |

FOREIGN PATENT DOCUMENTS

| | | | |
|---|---|---|---|
| WO | WO 2016/035035 | 3/2016 | |
| WO | WO-2016035035 A1 * | 3/2016 | ........ A61M 16/0051 |
| WO | WO 2016/133406 | 8/2016 | |
| WO | WO 2016/157106 | 10/2016 | |

OTHER PUBLICATIONS

Search Report and Written Opinion for European Application No. 17788927.6 dated Dec. 10, 2019, 7 pages.

* cited by examiner (A)

(B)

SYSTEM FOR DETERMINING AIRWAY PATENCY

TECHNICAL FIELD

The present disclosure generally relates to methods and/or apparatus and/or systems for monitoring a targeted gas being expired or being expelled from an apnoeic or non-spontaneously breathing patient and for determining if a patient's airway is blocked or if the airway has patency, and/or for determining which part of the patient's airway is blocked based on measurements of the targeted gas trace.

BACKGROUND

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in less than 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

If a patient's airway becomes occluded or obstructed (e.g. the airway may have collapsed or an item may have become lodged in the airway), then despite respiratory therapies which may be attempted for delivery to the patient for respiratory support, such therapies may be partially or wholly ineffective. In such situations, patient safety is compromised.

Reference to any prior art in this specification is not, and should not be taken as, an acknowledgement or any form of suggestion that that prior art forms part of the common general knowledge in the field of endeavour in any country in the world.

SUMMARY

It may be an object of certain embodiments disclosed herein to provide for a method and/or apparatus that might solve one or more of the above problems, or might go at least some way toward at least providing the public or medical profession with a useful choice.

The method or system or apparatus as disclosed herein may be associated with a flow therapy or respiratory support system or breathing circuits suitable for use with a patient.

Humidified gases can be used to allow for the comfortable gases delivery during the sedated stages of a patient (e.g. a patient that is undergoing a surgical procedure and has been sedated to the extent the patency of their airway may be compromised). Humidity prevents or helps to minimise the airways from drying out and hence can prevent or minimise damage to the airways and may also improve or assist with maintaining patient comfort when receiving a flow of gases being delivery to their airway(s). Such humidified gases may also be utilised for patients in alternative situations where for whatever reason the patient is apnoeic or non-spontaneously breathing.

In a first aspect there is provided a method or system for providing an indication or establishment of airway patency of a patient comprising:
 monitoring of at least one targeted gas that is being expired or being expelled from an airway of a patient, and
 based on measurements of the at least one targeted gas for a period of time, providing an indicator as to:
  a determination as to airway patency, or
  a determination as to a location of a blockage or obstruction in the airway, or
  a combination of i) and ii).

The monitoring of the at least one targeted gas may be by measuring or measurements of the variation in concentration of the at least one targeted gas.

The measuring or measurements may be obtained from one or more of:
 measurements taken adjacent or inside the mouth or oral cavity or oropharyngeal region of the patient,
 measurements taken adjacent or substantially adjacent the Pharynx, or a Pharyngeal flow of the patient,
 measurements taken adjacent or inside the nose or nasal cavity of the patient.

A determinable location of a blockage or obstruction in the airway may be the upper airway or the lower airway.

The targeted gas may be $CO_2$, $O_2$ or $N_2$ or a benign medical tracer gas or a gas indicative of the concentration of carbon dioxide, $O_2$ or $N_2$.

The targeted gas may be a tracer gas (or gases), and wherein the targeted gas may be one or more of: nitrogen or a nitrogen and oxygen mix, or helium or a helium and oxygen mix, or any other inert gas, or an inert gas and oxygen as a mixed gas), or may be any suitable gas can be used that is detectable and measureable may be used as a targeted gas.

The targeted gas may be included in the delivery of gases to the patient's airway as a part of a flow therapy or a respiratory support for the patient.

The targeted gas may be delivered to the patient's airway, and a concentration of said targeted gas may be measured or monitored for a period of time subsequent to the delivery.

Said expired or expelled gas or at least a portion of said expired or expelled gas is resultant due to cardiogenic activity or resultant due to the heart beat of a patient.

A flow therapy or respiratory support of a flow of gas may be delivered to the patient's airway via a patient interface wherein a said patient interface is of the type comprising a sealing or non-sealing interface, and may further comprise a nasal mask, an oral mask, an oro-nasal mask, a full face mask, a nasal pillows mask, a nasal cannula, a combination of the above or some other gas conveying patient interface system.

Said patient interface may deliver one or more of:
 a flow of gas to the patient's airway
 a targeted gas to a patient's airway.

The system or method may, further comprise:
 providing or delivering a flow therapy or respiratory support to a patient's airway for a period of time so as to increase oxygenation saturation of the patient
 removing or stopping or reducing the flow therapy or respiratory support being provided to the patient for a period of time providing or delivering a gas comprising a targeted gas to the patient's airway for a period of time restore provision or delivery of said flow therapy or respiratory support to the patient's airway measuring or taking measurements of the concentration of the targeted gas in expired or expelled gas from the patient for a period of time The oxygen saturation may be greater than about 95 or 96 or 97 or 98%), Removing or stopping or reducing the flow therapy or respiratory support may be, to reduce a pressure applied to the patient's airways or lungs by said flow therapy or respiratory support, or to allow the patient's lungs to partially deflate under reduced flow or pressure conditions relative to an initial flow or pressure conditions of the flow therapy or respiratory support previously provided or delivered to the patient), Providing or delivering a gas may be to at least partially reinflate the patient's lungs with said gas comprising said targeted gas), Measuring or taking measurements of the concentration may be, substantially without allowing said patient's lungs to deflate, Measuring or taking measurements of the concentration may comprise monitoring and tracking the variation in concentration of the targeted gas in expired or expelled gas from the patient for a period of time.

A sensor may be located adjacent or inside the mouth or oral cavity or oropharyngeal region of the patient to obtain measurements of the targeted gas being expired or expelled from the patient for a period of time.

The concentration of said targeted gas measured over time is correlated with the patient's heartbeat or cardiogenic action.

The flow therapy or respiratory support provided or delivered to the patient may be from a source of gases providing for a fraction of oxygen at greater than ambient or air conditions or greater than about 20.95% (on a dry weight basis) of oxygen, optionally the source of gases being up to about 100% oxygen gas. Optionally, said flow therapy or respiratory support gas(es) may be humidified.

The gas may comprise a targeted gas may be one or more of: a 50:50 mix of nitrogen to oxygen, a helium and oxygen mix, an inert gas or gases and oxygen mix, or any suitable gas that is detectable and measureable and which can be mixed with a breathable gas for the patient.

A gas provided or delivered to a said patient's airway may be humidified.

A flow therapy or a respiratory support may be provided or delivered to the patient's nares, and there is a measuring or taking of measurements of a pressure in a patient's airway (optionally, measuring or taking measurements of pressure using a sensor located above the larynx), optionally, a pressure in the patient's airway measured above the larynx of the patient contributes to a determination of patency of the pharyngeal airway.

The flow therapy or respiratory support may be provided or delivered via the patient's nare, a gas sensor being located at or adjacent or inside the mouth or oral cavity or oropharyngeal region of the patient to obtain measurements of the targeted gas being expired or expelled from the patient for a period of time, when the targeted gas is $CO_2$, and one or more of the following being measured:

wherein the concentration of $CO_2$ varies over time, the concentration of $CO_2$ measured by the gas sensor rising from a base concentration to a peak concentration and substantially returning to said base concentration, said peak concentration being in a substantially synchronous manner with the patient's heartbeat or cardiogenic activity (optionally, such a condition being indicative of a patient's soft palate or pharyngeal airway being patent or open and the patient's trachea being patent or open), wherein the concentration of $CO_2$ varies over time, the concentration of $CO_2$ measured by the gas sensor rising from a first base concentration to a first peak concentration and said $CO_2$ concentration reducing from said first peak concentration to a second base concentration greater than the first base concentration, and over a period of time (of more than 1 patient heart beat or cardiogenic activity) subsequent base concentrations returned to from subsequent peak concentrations being greater than a preceding base concentration over time and/or being substantially greater than the first base concentration over time, said first and second and subsequent peak concentrations being in substantially synchronous manner with the patient's heartbeat or cardiogenic activity (optionally, such a condition being indicative of a patient's soft palate or pharyngeal airway being closed or obstructed or occluded and the patient's trachea being patent or open), wherein the concentration of $CO_2$ does not vary over time or is of a non-varying concentration over time, the concentration of $CO_2$ measured by the gas sensor remaining at a base concentration, optionally said base concentration being in neither a synchronous or a non-synchronous manner with the patient's heart beat or cardiogenic activity The flow therapy or respiratory support may be provided or delivered via the patient's nare, a gas sensor being located at or inside the mouth or oral cavity or oropharyngeal region of the patient to obtain measurements of the targeted gas being expired or expelled from the patient for a period of time, and wherein after provision of the targeted gas to the patient, one or more of the following being measured:

wherein the concentration of the targeted gas varies over time, the concentration of the targeted gas measured by the gas sensor rising from a base concentration to a first peak concentration and substantially returning to said base concentration, and each subsequent peak concentration being substantially less or reduced relative to an immediately preceding peak concentration, each of said peak concentrations being in a substantially synchronous manner with the patient's heartbeat or cardiogenic activity (optionally, such a condition being indicative of a patient's soft palate or pharyngeal airway being patent or open and the patient's trachea being patent or open), wherein the concentration of the targeted gas varies over time, the concentration of targeted gas measured by the gas sensor rising from a first base concentration to a concentration substantially matching that of the targeted gas in gas ambient to the patient (e.g. air or operating theatre ambient gas conditions) and which is exposed to the gas sensor via the patient's oral cavity (optionally, such a condition being indicative of a patient's soft palate or pharyngeal airway being closed or obstructed or occluded and the patient's trachea being patent or open), wherein the concentration of the targeted gas reduces from an initial peak concentration to a base concentration, the concentration of the targeted gas measured by the gas sensor substantially remaining at a base concentration, optionally said base concentration being non-variant over time or being in neither a synchronous or a non-synchronous manner with the patient's heart beat or cardiogenic activity (optionally, such a condition being indicative of a patient's soft palate or pharyngeal airway being patent or open and the patient's trachea being closed or obstructed or occluded).

A flow therapy or a respiratory support may be provided at a constant flow rate.

A flow of gases may be provided or delivered to a patient's airway

Said flow of gases may be provided or delivered with an oscillating flow to the patient or superimposed oscillations of a positive gas flow to a patient may be delivered.

The oscillating flow may be delivered to accentuate and/or facilitate the expiration or expulsion of at least one targeted gas, such that the measurements of the at least one targeted gas for a period of time vary in response to the oscillating flow when the patients airway is unobstructed or patent.

The method may comprise determining a correlation between the delivered flow rate and said measurements of the at least one targeted gas as a monitored gas signal, and wherein said indicator is based on said correlation, optionally the monitored gas signal is based on the concentration of said targeted gas.

The flow may the sum of at least two oscillating waveforms (optionally the oscillating waveforms are substantially sinusoidal).

The flow may be substantially sinusoidal, optionally the flow signal is based on a sine function.

The flow may have one or more of the following signal characteristics: a frequency, optionally the frequency is substantially repeating over a period of time,
  an amplitude,
  a wave shape, or wave form, optionally the wave shape or wave form is substantially repeating over a period of time,
  a phase.

The correlation may be based on a comparison of one or more of:
  the frequency of the flow,
  the amplitude of the flow,
  the wave shape or wave form of the flow, optionally the wave shape or wave form is substantially repeating over a period of time,
  the phase of the flow,
  a change over time of the flow (for example a decay or driving of said flow),
  with one or more of:
  a frequency (or range of frequencies) of the monitored gas signal,
  an amplitude of the monitored gas signal,
  an amplitude of the monitored gas signal at a particular frequency,
  a wave shape or wave form of the monitored gas signal,
  a phase of the monitored gas signal,
  a change over time of the monitored gas signal.

The correlation may be based on a comparison of: the frequency of the flow, with a frequency (or range of frequencies) of the monitored gas signal, The correlation may be based on a comparison between one or more of:
  a signal edge or transition portion of the wave shape of the flow,
  a local maximum or minimum, or point of inflection of the wave shape of the flow,
  a gradient of a portion, or a gradient at a discrete point of the flow,
  a number of peaks and/or troughs of the flow in a given time period or a pre-determined time period
and one or more of:
  a subsequent signal edge or transition portion of the wave shape of the monitored gas signal, optionally, when the subsequent signal edge or transition portion of the wave shape of the monitored gas signal is located within a time period after the signal edge or transition portion of the wave shape of the flow,
  a subsequent local maximum or minimum, or point of inflection of the wave shape of the monitored gas signal optionally, when the subsequent local maximum or minimum of the wave shape of the monitored gas signal is located within a time period after the signal edge or transition portion of the wave shape of the flow,
  a subsequent gradient of a portion, or gradient at a discrete point of the wave shape of the monitored gas signal, optionally, when the subsequent gradient of a portion, or gradient at a discrete point of the wave shape of the monitored gas signal is located within a time period after the gradient of a portion, or the gradient at a discrete point the wave shape of the flow,
  a number of peaks and/or troughs of the monitored gas signal in a given time period or a pre-determined time period.

The signal edge may be one or more of:
  a rising edge or rising portion
  a falling edge or falling portion.

The patient's airway may be determined to be unobstructed or substantially unobstructed when the correlation between the delivered flow and said monitored gas signal is above a threshold.

The patient's airway may be determined to be unobstructed or substantially unobstructed when at least a component of a frequency (or range of frequencies) of the monitored gas signal is substantially matched to a frequency of the flow and when said matching of frequencies is above a threshold.

A level of patency of the patient's airway may be proportional to a strength of the correlation between the delivered flow and said monitored gas signal.

The patient's airway may be determined to be obstructed or substantially obstructed when the correlation between the delivered flow and said monitored targeted gas is below a threshold.

The patient's airway may be determined to be obstructed or substantially obstructed when at least a component of a frequency of the monitored gas signal is not similar to the frequency of the flow and/or when the amplitude of the signal at said frequency is similar and is below a threshold.

The monitored or targeted gas may be generated as a result of gas exchange in a patient's lungs, and wherein the flow acts to facilitate the expiration or expulsion of said monitored gas (optionally the patient is not spontaneously breathing), or to improve or accentuate gases exchange due to cardiogenic pulses occurring within the patient.

Said correlation may be determined by one or more of: a Monte-Carlo analysis, and/or a spectral analysis, and or a fast Fourier transform. In one form the correlation can be determined using a Sequential Monte Carlo analysis, and the correlation is used to determine an airway patency indication.

The measurements of the targeted gases may be instantaneously derived measurements, or real-time derived measurements.

The patient may be an apneoic or non-spontaneously breathing patient.

A signal or output may be provided, the signal or output associated individually with any one, or combinations of, said indicator.

The signal or may be is utilised to generate a warning or alarm, whether as one or combinations of one or more of: audible, haptic, visual.

The method or system may comprise a sensor, the sensor configured to detect an expired or expelled gas (such as said targeted gas) from a patient, optionally the sensor is a gas sensor or a capnography device.

A gas analyzer may be provided in communication with said gas sensor.

An electronic controller may be provided in communication with said gas sensor.

The electronic controller may determine the correlation between said targeted gas and said delivered flow rate.

The electronic controller may process said gas sensor or capnography device measurements or output(s) for determination of an expired or expelled gas waveform.

The controller may be further configured or adapted to process said gas sensor or capnography device measurements or output(s), said controller may be further configured or adapted to apply a correction factor or compensation to account for a particular flow rate of gas being delivered to the patient.

The flow therapy or respiratory support may be delivered to a patient's nare or nares (or the patient's nasal passage).

A said patient interface may be of the type comprising a sealing or non-sealing interface, and may further comprise a nasal mask, an oral mask, an oro-nasal mask, a full face mask, a nasal pillows mask, a nasal cannula, a combination of the above or some other gas conveying patient interface system.

The flow therapy or respiratory support may be delivered to the patient's airways is of a flow rate of: at least about 5, 10, 20, 30, 40, 50, 60, 70, 80, 90, 100, 110, 120, 130, 140, or 150 litres per min (LPM), or more; or may be selected between any of these values (for example, about 40 to about 80, about 50 to about 80, about 60 to about 80, about 70 to about 80 LPM); optionally, the gases supplied may be delivered in a fully saturated or humidified condition, or a saturated or humidified gas may be blended with other gases (whether being targeted gases or non-targeted gases) for supply or delivery to a patient interface or the patient, optionally, a targeted gas may be included in gases providing the flow therapy or respiratory support to the patient.

Thus, in accordance with a second aspect disclosed herein, there is provided a method or system for:

monitoring of at least one targeted gas (e.g. CO2, N2 or may be other gases capable of being detected, monitored, and measured) that is being expired or being expelled from an airway of a patient (e.g. an apnoeic or non-spontaneously breathing patient), and based on measurements of the at least one targeted gas for a period of time, providing an indicator as to:
i. an output of the measurements of the at least one targeted gas for the period of time, or
ii. a determination as to airway patency, or
iii. a determination as to a location of a blockage or obstruction in the airway, or
iv. a combination of i) and ii), or
v. a combination of i) and iii), or
vi. a combination of ii) and iii) or
vii. a combination of i) and ii) and iii).

For item i) the output may be a display of the targeted gas trace. Optionally, such a trace may be displayed on a user interface such as a screen (e.g. a GUI) and may be updated either in real-time or at an appropriate refresh rate so as to ensure a clinician is provided with information relating to the output of a said targeted gas.

The monitoring of the at least one targeted gas may be by measuring or measurements of the variation in concentration of the at least one targeted gas.

The measuring or measurements may be obtained from one or more of:
measurements taken at or inside the mouth or oral cavity or oropharyngeal region of the patient,
measurements taken at or substantially adjacent the Pharynx, or a Pharyngeal flow of the patient,
measurements taken at or inside the nose or nasal cavity of the patient.

A signal or output may be provided, the signal or output associated individually with any one, or combinations of, i)-vii).

The signal or output may be utilised to generate a warning or alarm, whether as one or combinations of one or more of: audible, haptic, visual. For example, an audible alarm may sound, or a vibration may be initiated for a user-wearable device, or a light may flash or be switched on or off or a graphical user interface (GUI) may be provided with an image. Such warning or alarms may be utilised to alert a medical professional or an assistant to a change in status of i) or ii) or iii) (e.g. a patient's airway may be patent but may collapse or become obstructed and lose patency, or the location of a blockage or obstruction inn a patient's airway may change which may have ramifications to the medical professionals working on the patient or responsible for respiratory support for the patient). For example, if a blockage or a patient's airway is determined, then an alarm or warning can be raised to alert or inform those associated with the patient's care.

A warning or alarm or indication may be raised related to the patency of a patient's airway, such as for example if an airway occlusion or blockage or obstruction is detected or if the patency of a said patient's airway is compromised. Optionally, there may be different warnings or alarms or indications provided relating to different locations of such an occlusion or blockage or obstruction, for example if the upper airway is occluded or blocked or obstructed there may be a warning or alarm or indication, such as a first sound or first haptic or first visual output, and if the lower airway is occluded or blocked or obstructed there may be a second alarm warning or alarm or indication, such as a second sound or second haptic or second visual output.

A determinable location of a blockage or occlusion or obstruction in the airway may be the upper airway or the lower airway.

Optionally, a determination may be made of additional or different locations of a blockage or occlusion or obstruction based on a processing of the output of a targeted gas or a tracer gas.

The targeted gas may be CO2 or N2 or a benign medical tracer gas (e.g. Argon), or another gas or gases capable of being detected and measured for the purposes of determining a trace indication of the targeted gas for a period of time. Optionally, any suitable inert gas can be used as a tracer gas such as Helium or Argon or Neon providing the gas is non-toxic and such a gas is not so dense that it remains within the lungs. Suitable targeted gases may be delivered as a mixture of O2 and the inert gas.

The targeted gas may be a tracer gas (or gases) such as a nitrogen (for example of a nitrogen and oxygen mix) or helium (for example of a helium and oxygen mix) or may be any other inert gas (for example, such an inert gas and oxygen as a mixed gas). Alternatively, any suitable gas can be used that is detectable and measureable may be used as a targeted gas.

The targeted gas may be included in the delivery of gases to the patient's airway as a part of a flow therapy or a respiratory support for the patient.

The targeted gas may be delivered to the patient's airway, and a concentration of said targeted gas may be measured or monitored for a period of time subsequent to the delivery. Optionally, such a period of time may be an entire period of time the patient is provided with a flow therapy or respiratory support, or may be an entire period of time a patient is apnoeic or non-spontaneously breathing.

The concentration of the targeted gas for a period of time may be analyzed and based on the analysis, a determination may be made as to airway patency and/or the location of a blockage or obstruction in the airway is determined.

The method or system may comprising a sensor, the sensor may be configured to detect an expired or expelled gas (e.g. said targeted gas) from a patient. Optionally, the sensor may be a gas sensor or a capnography device.

A gas analyzer may be provided in communication with said gas sensor.

A controller may be provided in communication with said gas sensor.

The controller may process said gas sensor or capnography device measurements or output(s) for determination of an expired or expelled gas waveform.

The controller may be further configured or adapted to process said gas sensor or capnography device measurements or output(s), said controller further configured or adapted to apply a correction factor or compensation to account for a particular flow rate of gas being delivered to the patient. For example, particular flow rates of gas being delivered to the patient, if sufficiently high, can interfere with or add 'noise' to the signal or output generated by the sensor in response to sensing or detecting the expired or expelled gas from a patient.

The method or system may provide for compensation to account for a flow rate of gas being delivered to the patient's airways from interfering or adding noise to measurements or sensing of an expired or expelled gas (e.g. targeted gas) from the patient.

Said expired or expelled gas may be resultant due to cardiogenic activity or resultant due to the heart beat of a patient.

A flow therapy or respiratory support of a flow of gas may be delivered to the patient's airway A said targeted gas may be delivered to the patient's airways via a patient interface as a part of a flow therapy or respiratory support of a flow of gas being delivered to the patient's airway.

The flow therapy or respiratory support may be delivered to a patient's nare or nares (or the patient's nasal passage). Alternatively or in addition, the flow therapy or respiratory support is delivered to a patient's oral cavity.

Optionally, the patient interface may comprise a sealing or non-sealing interface, and may comprise a nasal mask, an oral mask, an oro-nasal mask, a full face mask, a nasal pillows mask, a nasal cannula, a combination of the above or some other gas conveying system.

The flow therapy or respiratory support delivered to the patient's airways may be of a flow rate of: at least about 5, 10, 20, 30, 40, 50, 60, 70, 80, 90, 100, 110, 120, 130, 140, or 150 litres per min (LPM), or more; or may be selected between any of these values (for example, about 40 to about 80, about 50 to about 80, about 60 to about 80, about 70 to about 80 LPM); optionally, the gases supplied may be delivered in a fully saturated or humidified condition, or a saturated or humidified gas may be blended with other gases (whether being targeted gases or non-targeted gases) for supply or delivery to a patient interface or the patient. Optionally, a targeted gas may be included in gases providing the flow therapy or respiratory support to the patient.

In relation to the method or system as disclosed herein, the flow rate of gases provided by a flow therapy or a respiratory support may be a constant flow rate, but alternatively oscillating or cyclic flow may be provided.

The method or system may comprise:
providing or delivering a flow therapy or respiratory support to a patient's airway for a period of time so as to increase oxygenation saturation of the patient (optionally, to an oxygen saturation of greater than about 95 or 96 or 97 or 98%),
removing or stopping or reducing the flow therapy or respiratory support being provided to the patient for a period of time (optionally, to reduce a pressure applied to the patient's airways or lungs by said flow therapy or respiratory support, or to allow the patient's lungs to partially deflate under reduced flow or pressure conditions relative to an initial flow or pressure conditions of the flow therapy or respiratory support previously provided or delivered to the patient),
providing or delivering a gas comprising a targeted gas to the patient's airway for a period of time (optionally, to at least partially reinflate the patient's lungs with said gas comprising said targeted gas),
restore provision or delivery of said flow therapy or respiratory support to the patient's airway (optionally, substantially without allowing said patient's lungs to deflate),
measuring or taking measurements of the concentration of the targeted gas in expired or expelled gas from the patient for a period of time (optionally monitoring and tracking the variation in concentration of the targeted gas in expired or expelled gas from the patient for a period of time).

A sensor may be located at or inside the mouth or oral cavity or oropharyngeal region of the patient to obtain measurements of the targeted gas being expired or expelled from the patient for a period of time.

The concentration of said targeted gas measured over time may be correlated with the patient's heartbeat or cardiogenic action.

The flow therapy or respiratory support provided or delivered to the patient may be from a source of gases providing for a fraction of oxygen at or greater than about 90%, alternatively the source of gases may be air. Optionally the source of gases may be supplemented with additional oxygen. Optionally, said flow therapy or respiratory support gas(es) may be humidified.

The gas comprising a targeted gas may be a 50:50 mix of nitrogen to oxygen. Alternatively, may be a helium and oxygen mix, may be or any other inert gas and oxygen mix. Alternatively, any suitable gas can be used that is detectable and measureable which may be mixed with a breathable gas for the patient. Alternatively, the targeted gas could be a gas mix with less than about 50% O2 with a minimum of about 5% O2. Optionally, said gas comprising the targeted gas may be humidified.

The flow therapy or respiratory support may be provided or delivered to the patient's nares, and measuring or taking measurements of a pressure in a patient's airway (optionally, measuring or taking measurements of pressure using a sensor located above the larynx). Optionally, a pressure in the patient's airway measured above the larynx of the patient contributes to a determination of patency of the pharyngeal airway.

The flow therapy or respiratory support may be provided or delivered via the patient's nare, a gas sensor may be located at or inside the mouth or oral cavity or oropharyngeal region of the patient to obtain measurements of the targeted gas being expired or expelled from the patient for a period of time, when the targeted gas is CO2, and one or more of the following being measured:

wherein the concentration of CO2 varies over time, the concentration of CO2 measured by the gas sensor rising from a base concentration to a peak concentration and substantially returning to said base concentration, said peak concentration being in a substantially synchronous manner with the patient's heartbeat or cardiogenic activity (optionally, such a condition being indicative of a patient's soft palate or pharyngeal airway being patent or open and the patient's trachea being patent or open), wherein the concentration of CO2 varies over time, the concentration of CO2 measured by the gas sensor rising from a first base concentration to a first peak concentration and said CO2 concentration reducing from said first peak concentration to a second base concentration greater than the first base concentration, and over a period of time (of more than 1 patient heart beat or cardiogenic activity) subsequent base concentrations returned to from subsequent peak concentrations being greater than a preceding base concentration over time and/or being substantially greater than the first base concentration over time, said first and second and subsequent peak concentrations being in substantially synchronous manner with the patient's heartbeat or cardiogenic activity (optionally, such a condition being indicative of a patient's soft palate or pharyngeal airway being closed or obstructed or occluded and the patient's trachea being patent or open), wherein the concentration of CO2 does not vary over time or is of a non-varying concentration over time, the concentration of CO2 measured by the gas sensor remaining at a base concentration, optionally said base concentration being in neither a synchronous or a non-synchronous manner with the patient's heart beat or cardiogenic activity (optionally, such a condition being indicative of a patient's soft palate or pharyngeal airway being patent or open and the patient's trachea being closed or obstructed or occluded).

The targeted gas may be a gas which is not consumed by a patient or their respiratory system.

The flow therapy or respiratory support may be provided or delivered via the patient's nare, a gas sensor may be located at or inside the mouth or oral cavity or oropharyngeal region of the patient to obtain measurements of the targeted gas being expired or expelled from the patient for a period of time, and wherein after provision of the targeted gas to the patient, one or more of the following being measured:

wherein the concentration of the targeted gas varies over time, the concentration of the targeted gas measured by the gas sensor rising from a base concentration to a first peak concentration and substantially returning to said base concentration, and each subsequent peak concentration being substantially less or reduced relative to an immediately preceding peak concentration, each of said peak concentrations being in a substantially synchronous manner with the patient's heartbeat or cardiogenic activity (optionally, such a condition being indicative of a patient's soft palate or pharyngeal airway being patent or open and the patient's trachea being patent or open), wherein the concentration of the targeted gas varies over time, the concentration of targeted gas measured by the gas sensor rising from a first base concentration to a concentration substantially matching that of the targeted gas in gas ambient to the patient (e.g. air or operating theatre ambient gas conditions) and which is exposed to the gas sensor via the patient's oral cavity (optionally, such a condition being indicative of a patient's soft palate or pharyngeal airway being closed or obstructed or occluded and the patient's trachea being patent or open)

wherein the concentration of the targeted gas reduces from an initial peak concentration to a base concentration, the concentration of the targeted gas measured by the gas sensor substantially remaining at a base concentration, optionally said base concentration being non-variant over time or being in neither a synchronous or a non-synchronous manner with the patient's heart beat or cardiogenic activity (optionally, such a condition being indicative of a patient's soft palate or pharyngeal airway being patent or open and the patient's trachea being closed or obstructed or occluded).

The flow therapy or respiratory support may be delivered at a constant flow rate. Alternatively, the flow therapy or respiratory support may be delivered with an oscillating (positive) flow rate to the patient or superimposed oscillations may be delivered. Optionally, an oscillations flow is delivered to accentuate the expiration of CO2 or tracer gases.

According to the disclosure herein, a high flow gas delivered by a high flow therapy or respiratory support method or apparatus can be generated to comprise various components with one or more parameters (e.g. flow rate) that can be adjusted, including being adjusted to oscillate. Each parameter might be adjusted independently, or in dependence on other parameters. This provides a varying gas flow (varying gas flow parameters). The varying gas flow (with oscillations) assists with gas removal (e.g. expired or expelled CO2 or other gases, including for example targeted gas or benign tracer gas removal) and can assist with oxygenation or the provision or delivery of other gases (e.g. targeted gas or benign tracer gas) to a patient's airway or respiratory system. As an example, the gas flow could comprise a base flow rate component that does not vary, combined with one or more oscillating flow rate components, each at different frequencies. This generates an overall gas flow waveform that varies. The flow therapy apparatus can be controlled through valves, blower controller and/or other modulating devices to generate the flow rate components. PCT application PCT/IB2016/051820 describes the use of oscillating components and is incorporated herein in its entirety.

The method or system may comprise a high flow gases source, a proportional valve to create oscillating waveforms, or an oscillator arrangement. Optionally, the system may additionally comprise a controller to control the proportional valve or gases source or humidifier.

As relatively high gas delivery flow rates may be used with the embodiments or configurations described herein, the gases being supplied or delivered to the user or patient may be delivered to different parts of the user's or a patient's airway. The gases being supplied may reach the patient's lungs or any part of the respiratory system.

For example, according to those various embodiments described herein, a flow rate of gases supplied or provided to an interface or via a system, such as for provision of a flow therapy or a respiratory support, may comprise, but is not limited to, flows of at least about 5, 10, 20, 30, 40, 50, 60, 70, 80, 90, 100, 110, 120, 130, 140, or 150 litres per min (LPM), or more, and useful ranges may be selected between any of these values (for example, about 40 to about 80, about 50 to about 80, about 60 to about 80, about 70 to about 80 LPM). Optionally, the gases supplied may be delivered in a fully saturated or humidified condition, or a saturated or humidified gas may be blended with other gases for supply or delivery to a patient interface or the patient.

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

Said flow of gases may be an oscillating flow of gases On a falling edge (or a falling flow rate) of the oscillating flow the pressure in a patients airway decreases, and
  wherein if the patient's airway is at least partially patent a targeted gas is expelled from the patient's airway or the targeted gas is detected in gas expelled from the patient's airway,
  wherein if the patient's airway is patent substantially no targeted gas is expelled from the patient's airway or there is no detection of the targeted gas expelled from a patient's airway.

An amplitude, or rise time (or rising gradient), or fall time (or falling gradient) of the concentration of the targeted gas corresponds to the degree to which the patient's airway is patent.

The method or system comprises measuring a concentration of a targeted gas, and wherein the patient's airway is determined to be at least partially patent when the concentration of the gases increases after said falling edge (or falling flow rate or falling pressure).

The concentration of said targeted gas may be measured in a period between two flow peaks of the oscillating flow (or oscillating pressure?).

The concentration of a targeted gas may be measured between subsequent pairs of flow (or pressure) peaks of said oscillating flow (or oscillating pressure).

The provided or delivered oscillating (positive) flow rate (or pressure of a flow) may have one or more of the following oscillation characteristics:
  amplitude,
  frequency (or period),
  wavelength.

The oscillation characteristics may vary with respect to time.

The determination of airway patency may be based on a correlation factor, the correlation factor being based on a comparison between the oscillation characteristics of the oscillating flow, and one or more targeted gas characteristics.

The targeted gas characteristics may be relate to the concentration (or an indicator thereof) of the targeted gas.

The targeted gas characteristic(s) may be measured instantaneously or are real-time measurements.

The targeted gas characteristic(s) may be measured at a time corresponding to a trough, or a point between two peaks, of the oscillating flow rate (or oscillation pressure of the delivered flow).

The targeted gas characteristic(s) may be measured over a time period.

The targeted gas characteristics may change with respect to time.

The targeted gas characteristics may be one or more of:
  amplitude,
  frequency (or period),
  wavelength,
  phase.

The tracer gas may be introduced to the oscillating flow for a first period of time, after said first period the introduction of the tracer gas is ceased and the concentration of the tracer gas measured over a second period of time.

The determination of airway patency may be based on one or more of:
  a comparison or correlation between said oscillation characteristics of said oscillating flow (or oscillating pressure of the flow delivered) and target gas characteristics of said target gas (optionally over said second period of time).
  a rate of decay of the concentration of the targeted gas concentration over said second period of time.

In a third aspect of the invention there is provided a method of determining a state of an airway of a patient, the method comprising:
  delivering an flow (or optionally pressure) of gases to a patient, said flow of gases delivered in accordance with a flow signal, and
  monitoring the concentration of at least one gas that is being expired or being expelled from an airway of a patient, as a monitored gas signal, and determining a correlation between the delivered flow signal and said monitored gas signal, and characterizing a state of the patient's airway based on said correlation.

Said flow may be an oscillating flow.

Said flow may vary over time.

Said flow may comprises a flow offset or bias.

Said flow signal may be delivered with a first shape or profile (optionally the shape or profile is repeating), and wherein the correlation is based on a comparison of said first shape or profile of the flow signal and a second shape or profile (or subsequent shape or profile) of the monitored gas signal.

Said correlation may be based on a comparison between a waveform property of the flow signal, and a waveform property of the monitored gas signal.

Said flow may be configured to improve or accentuate gases exchange due to cardiogenic pulses occurring within the patient.

The flow signal may be the sum of at least two oscillating waveforms (optionally the oscillating waveforms are substantially sinusoidal.)

The flow signal may be substantially sinusoidal, optionally the flow signal is based on a sine function.

The flow signal may have one or more of the following signal characteristics:
  a frequency, optionally the frequency is substantially repeating over a period of time,
  an amplitude,
  a wave shape, or wave form, optionally the wave shape or wave form is substantially repeating over a period of time,
  a phase.

The correlation may be based on a comparison of one or more of:
the frequency of the flow signal,
the amplitude of the flow signal,
the wave shape or wave form of the flow signal, optionally the wave shape or wave form is substantially repeating over a period of time,
the phase of the flow signal,
a change over time of the flow signal (for example a decay or driving of said signal),
to one or more of:
a frequency (or range of frequencies) of the monitored gas signal,
an amplitude of the monitored gas signal,
an amplitude of the monitored gas signal at a particular frequency,
a wave shape or wave form of the monitored gas signal,
a phase of the monitored gas signal,
a change over time of the monitored gas signal.

The correlation may be based on a comparison between one or more of:
a signal edge or transition portion of the wave shape of the flow signal,
a local maximum or minimum, or point of inflection of the wave shape of the flow signal
a gradient of a portion, or a gradient at a discrete point of the flow signal
a number of peaks and/or troughs of the flow signal in a given time period or a pre-determined time period
and one or more of:
a subsequent signal edge or transition portion of the wave shape of the monitored gas signal, optionally, when the subsequent signal edge or transition portion of the wave shape of the monitored gas signal is located within a time period after the signal edge or transition portion of the wave shape of the flow signal,
a subsequent local maximum or minimum, or point of inflection of the wave shape of the monitored gas signal optionally, when the subsequent local maximum or minimum of the wave shape of the monitored gas signal is located within a time period after the signal edge or transition portion of the wave shape of the flow signal,
a subsequent gradient of a portion, or gradient at a discrete point of the wave shape of the monitored gas signal, optionally, when the subsequent gradient of a portion, or gradient at a discrete point of the wave shape of the monitored gas signal is located within a time period after the gradient of a portion, or the gradient at a discrete point the wave shape of the flow signal,
a number of peaks and/or troughs of the monitored gas signal in a given time period or a pre-determined time period.

The signal edge may be one or more of:
a rising edge or rising portion
a falling edge or falling portion.

The patient's airway may be determined to be unobstructed or substantially unobstructed when the correlation between the delivered flow and said monitored gas signal is above a threshold.

The patient's airway may be determined to be unobstructed or substantially unobstructed when at least a component of a frequency (or range of frequencies) of the monitored gas signal is similar to a frequency (or range of frequencies) of the flow signal and when the amplitude of the flow signal at said frequency is above a threshold.

The patient's airway may be determined to be unobstructed or substantially unobstructed when at least a component of a frequency (or range of frequencies) of the monitored gas signal is substantially matched to a frequency of the flow signal and when said matching of frequencies is above a threshold. A level of patency of the patient's airway may be proportional to a strength of the correlation between the delivered flow signal and said monitored gas signal.

The patient's airway may be determined to be obstructed or substantially obstructed when the correlation between the delivered flow and said monitored targeted gas is below a threshold.

The patient's airway may be determined to be unobstructed or substantially unobstructed when at least a component of a frequency of the monitored gas signal is similar to the frequency of the flow signal and when the amplitude of the signal at said frequency is above a threshold.

The monitored gas signal may be measured instantaneously, or in real-time, or is sampled (optionally at regular intervals).

Said flow may be configured to create a flow of gases from the patient to facilitate the expiration or expulsion of said gas.

Parameters of said flow may be selected to optimize or increase the expiration or expulsion of said gas from said patient.

The monitored gas signal may be based on the concentration (or an indicator thereof) of the monitored gas.

The state of the patients airway is one or more of:
a determination as to airway patency, and/or
a determination as to a location of a blockage or obstruction in the airway.

A determinable location of a blockage or obstruction in the airway may be the upper airway or the lower airway.

The monitored gas may be one of: CO2 or O2, or a gas indicative of the concentration of carbon dioxide or O2.

The monitored gas signal may be obtained from one or more of:
measurements taken at or inside the mouth or oral cavity or oropharyngeal region of the patient,
measurements taken at or substantially adjacent the Pharynx, or a Pharyngeal flow of the patient,
measurements taken at or inside the nose or nasal cavity of the patient.

The monitored gas (e.g. a targeted gas) is generated as a result of gas exchange in a patient's lungs, and wherein the flow acts to facilitate the expiration or expulsion of said monitored gas (optionally the patient is not spontaneously breathing.)

The flow may be delivered via a patient interface

A said patient interface may be of the type comprising a sealing or non-sealing interface.

Said patient interface may comprise a nasal mask, an oral mask, an oro-nasal mask, a full face mask, a nasal pillows mask, a nasal cannula, a combination of the above or some other gas conveying patient interface system.

The flow therapy or respiratory support delivered to the patient's airways may be of an average flow rate of: at least about 5, 10, 20, 30, 40, 50, 60, 70, 80, 90, 100, 110, 120, 130, 140, or 150 litres per min (LPM), or more; or may be selected between any of these values (for example, about 40 to about 80, about 50 to about 80, about 60 to about 80, about 70 to about 80 LPM);

The gases supplied may be delivered in a fully saturated or humidified condition, or a saturated or humidified gas may be blended with other gases (whether being targeted gases or non-targeted gases) for supply or delivery to a patient interface or the patient, optionally, a medical gas may be included in gases providing the flow therapy or respiratory support to the patient.

Said correlation may be determined by one or more of: a Monte-Carlo analysis, and/or a spectral analysis. In one form a Sequential Monte Carlo method can be used.

In a fourth aspect of the invention there is provided an apparatus, the apparatus may comprise a flow generator to provide a flow of gases (optionally an oscillating flow) to be delivered to a patient in accordance with a flow signal, a gas sensor (or sampling device) configured to monitor or detect at least one parameter (optionally concertation) of targeted gas as a monitored gas signal (e.g. CO2, N2 or may be other gases capable of being detected, monitored, and measured) that is being expired or being expelled from an airway of a patient (e.g. an apnoeic or non-spontaneously breathing patient), and a controller (optionally comprising a processor) for determining a correlation between the delivered flow signal and said monitored gas signal, and characterizing a state of the patient's airway based on said correlation.

The indicator may be based on measurements of the at least one targeted gas for a period of time (or instantaneously).

The sensor may be a gas sensor or a capnography device.

The apparatus may further comprise a gas analyzer is provided in communication with said gas sensor.

An electronic controller may be provided in communication with said gas sensor.

The electronic controller may process said gas sensor or capnography device measurements or output(s) for determination of an expired or expelled gas waveform.

The controller may be further configured or adapted to process said gas sensor or capnography device measurements or output(s), said controller further configured or adapted to apply a correction factor or compensation to account for a particular flow rate of gas being delivered to the patient.

The gas sensor or sampling device may be part of a patient interface arrangement.

The sampling device may comprise a sampling tip to sample said gas, the sampling tip being in communication with a gas sensor The apparatus may further comprise a capnography device or unit and/or said gas sensor.

In a fifth aspect there is provided an apparatus (or apparatus assembly) for determining airway patency, the apparatus comprising:

a flow generator to provide an flow of a flow of gas to be delivered to a patient, said flow of gases delivered in accordance with an flow signal a gas sensor configured to monitor a concentration of at least one gas, to provide for a monitored gas signal and a controller (optionally comprising a processor) for:
determining a correlation between the delivered flow signal and said monitored gas signal
characterising a state of the patient's airway based on said correlation.

The sensor may be a gas sensor or a capnography device.

A gas analyzer may be provided in communication with said gas sensor.

An electronic controller may be provided in communication with said gas sensor.

The electronic controller may process said gas sensor or capnography device measurements or output(s) for determination of an expired or expelled gas waveform.

The controller may be further configured or adapted to process said gas sensor or capnography device measurements or output(s), said controller further configured or adapted to apply a correction factor or compensation to account for a particular flow rate of gas being delivered to the patient.

The gas sensor or sampling device may be part of a patient interface arrangement.

The sampling device may comprise a sampling tip to sample said gas, the sampling tip being in communication with a gas sensor The apparatus may further comprise a capnography device or unit and/or said gas sensor.

With respect to both the fourth and fifth aspects the following options are provided.

In particular, with respect to the apparatus as described herein in relation to the fourth and fifth aspects, the options described below are provided for:

The controller may monitor the at least one targeted gas is by measuring or measurements of the variation in concentration of the at least one targeted gas, optionally the measurements are made by the sampling device (optionally comprising a gas sensor).

The sampling device may take measurements from one or more of:
measurements taken adjacent or inside the mouth or oral cavity or oropharyngeal region of the patient,
measurements taken adjacent or substantially adjacent the Pharynx, or a Pharyngeal flow of the patient,
measurements taken adjacent or inside the nose or nasal cavity of the patient.

The controller may determine a location of a blockage or obstruction in the airway, the location may be the upper airway or the lower airway.

The targeted gas is CO2, O2 or N2 or a benign medical tracer gas or a gas indicative of the concentration of carbon dioxide, O2 or N2.

The targeted gas may be added to the gases provided to the patient's airway as a part of a flow therapy or a respiratory support for the patient by the flow generator.

The targeted gas may delivered to the patient's airway by a patient interface, and a concentration of said targeted gas is measured or monitored for a period of time subsequent to the delivery by the sampling device.

Said expired or expelled gas or at least a portion of said expired or expelled gas may be resultant due to cardiogenic activity or resultant due to the heart beat of a patient.

A flow therapy or respiratory support of a flow of gas may be delivered to the patient's airway via a patient interface wherein a said patient interface is of the type comprising a sealing or non-sealing interface, and may further comprise a nasal mask, an oral mask, an oro-nasal mask, a full face mask, a nasal pillows mask, a nasal cannula, a combination of the above or some other gas conveying patient interface system.

Said patient interface may deliver one or more of:
a flow of gas to the patient's airway
a targeted gas to a patient's airway.

The controller may be configured to:
control the flow generator to provide or deliver a flow therapy or respiratory support to a patient's airway for a period of time so as to increase oxygenation saturation of the patient
remove or stop or reduce the flow therapy or respiratory support being provided to the patient for a period of time control the flow generator to provide or deliver a gas comprising a targeted gas to the patient's airway for a period of time control the flow generator to restore provision or delivery of said flow therapy or respiratory support to the patient's airway to measure or take measurements of the concentration of the targeted gas in expired or expelled gas from the patient for a period of time.

The controller may be configured to correlation the concentration of said targeted gas measured over time with the patient's heartbeat or cardiogenic action.

The apparatus may be configured to deliver the flow therapy or respiratory support via the patient's nare, the gas sensor (optionally part of the sampling device) being located at or inside the mouth or oral cavity or oropharyngeal region of the patient to obtain measurements of the targeted gas being expired or expelled from the patient for a period of time, when the targeted gas is CO2, and the controller may be configured to detect one or more of the following:

wherein the concentration of CO2 varies over time, the concentration of CO2 measured by the gas sensor rising from a base concentration to a peak concentration and substantially returning to said base concentration, said peak concentration being in a substantially synchronous manner with the patient's heartbeat or cardiogenic activity, wherein the concentration of CO2 varies over time, the concentration of CO2 measured by the gas sensor rising from a first base concentration to a first peak concentration and said CO2 concentration reducing from said first peak concentration to a second base concentration greater than the first base concentration, and over a period of time (of more than 1 patient heart beat or cardiogenic activity) subsequent base concentrations returned to from subsequent peak concentrations being greater than a preceding base concentration over time and/or being substantially greater than the first base concentration over time, said first and second and subsequent peak concentrations being in substantially synchronous manner with the patient's heartbeat or cardiogenic activity, wherein the concentration of CO2 does not vary over time or is of a non-varying concentration over time, the concentration of CO2 measured by the gas sensor remaining at a base concentration.

The flow therapy or respiratory support may be provided or delivered via the patient's nare, the gas sensor (optionally being part of said sampling device) located at or inside the mouth or oral cavity or oropharyngeal region of the patient to obtain measurements of the targeted gas being expired or expelled from the patient for a period of time, and wherein after provision of the targeted gas to the patient, the controller may be configured to detect one or more of the following:

wherein the concentration of the targeted gas varies over time, the concentration of the targeted gas measured by the gas sensor rising from a base concentration to a first peak concentration and substantially returning to said base concentration, and each subsequent peak concentration being substantially less or reduced relative to an immediately preceding peak concentration, each of said peak concentrations being in a substantially synchronous manner with the patient's heartbeat or cardiogenic activity wherein the concentration of the targeted gas varies over time, the concentration of targeted gas measured by the gas sensor rising from a first base concentration to a concentration substantially matching that of the targeted gas in gas ambient to the patient (e.g. air or operating theatre ambient gas conditions) and which is exposed to the gas sensor via the patient's oral cavity, wherein the concentration of the targeted gas reduces from an initial peak concentration to a base concentration, the concentration of the targeted gas measured by the gas sensor substantially remaining at a base concentration, optionally said base concentration being non-variant over time or being in neither a synchronous or a non-synchronous manner with the patient's heart beat or cardiogenic activity.

A flow of gases is provided or delivered to a patient's airway by a patient interface.

The flow generator may be configured to provide a flow of gases with an oscillating flow to the patient or superimposed oscillations of a positive gas flow to a patient may be delivered.

The flow generator may be configured to provide an oscillating flow delivered to accentuate and/or facilitate the expiration or expulsion of at least one targeted gas, such that the measurements of the at least one targeted gas for a period of time vary in response to the oscillating flow when the patients airway is unobstructed or patent.

The method may comprise determining a correlation between the delivered flow rate and said measurements of the at least one targeted gas as a monitored gas signal, and wherein said indicator is based on said correlation.

The flow generator may be configured to provide flow based on a flow signal provided by the controller, the flow having one or more of the following signal characteristics:

a frequency, optionally the frequency is substantially repeating over a period of time, an amplitude, a wave shape, or wave form, optionally the wave shape or wave form is substantially repeating over a period of time, a phase.

The controller may be configured to determine the correlation based on a comparison of one or more of:

the frequency of the flow, the amplitude of the flow, the wave shape or wave form of the flow, optionally the wave shape or wave form is substantially repeating over a period of time, the phase of the flow, a change over time of the flow (for example a decay or driving of said flow), with one or more of:

a frequency (or range of frequencies) of the monitored gas signal, an amplitude of the monitored gas signal, an amplitude of the monitored gas signal at a particular frequency, a wave shape or wave form of the monitored gas signal, a phase of the monitored gas signal, a change over time of the monitored gas signal.

The controller may be configured to determine the correlation based on a comparison of: the frequency of the flow, with a frequency (or range of frequencies) of the monitored gas signal.

The controller may be configured to determine the correlation based on a comparison between one or more of:

a signal edge or transition portion of the wave shape of the flow, a local maximum or minimum, or point of inflection of the wave shape of the flow, a gradient of a portion, or a gradient at a discrete point of the flow, a number of peaks and/or troughs of the flow in a given time period or a pre-determined time period
and one or more of:
a subsequent signal edge or transition portion of the wave shape of the monitored gas signal, optionally, when the subsequent signal edge or transition portion of the wave shape of the monitored gas signal is located within a time period after the signal edge or transition portion of the wave shape of the flow,
a subsequent local maximum or minimum, or point of inflection of the wave shape of the monitored gas signal optionally, when the subsequent local maximum or minimum of the wave shape of the monitored gas signal is located within a time period after the signal edge or transition portion of the wave shape of the flow,
a subsequent gradient of a portion, or gradient at a discrete point of the wave shape of the monitored gas signal, optionally, when the subsequent gradient of a portion, or gradient at a discrete point of the wave shape of the monitored gas signal is located within a time period after the gradient of a portion, or the gradient at a discrete point the wave shape of the flow,
a number of peaks and/or troughs of the monitored gas signal in a given time period or a pre-determined time period.

The controller may determine the patient's airway to be unobstructed or substantially unobstructed when the correlation between the delivered flow and said monitored gas signal is above a threshold.

The controller may determine the patient's airway to be unobstructed or substantially unobstructed when at least a component of a frequency (or range of frequencies) of the monitored gas signal is substantially matched to a frequency of the flow and when said matching of frequencies is above a threshold.

The controller may determine a level of patency of the patient's airway, said level being proportional to a strength of the correlation between the delivered flow and said monitored gas signal.

The controller may determine the patient's airway to be obstructed or substantially obstructed when the correlation between the delivered flow and said monitored targeted gas is below a threshold.

The controller may determine the patient's airway to be obstructed or substantially obstructed when at least a component of a frequency of the monitored gas signal is not similar or is different or is sufficiently dissimilar to the frequency of the flow and/or when the amplitude of the signal at said frequency is similar and is below a threshold.

The monitored or targeted gas is generated as a result of gas exchange in a patient's lungs, and wherein the flow provided by said flow generator acts to facilitate the expiration or expulsion of said monitored gas (optionally the patient is not spontaneously breathing), or to improve or accentuate gases exchange due to cardiogenic pulses occurring within the patient.

The controller may determine said correlation by one or more of: a Monte-Carlo analysis, and/or a spectral analysis, and/or a fast Fourier transform.

It will be appreciated that the apparatuses of the fourth and fifth aspects may perform the method of any of the first to third aspects. As such any alternatives as described with respect to the first to third aspects are applicable to the fourth and fifth aspects.

In a sixth aspect there is provided a method or system for providing an indication or establishment of airway patency of a patient comprising:

providing or delivering a flow rate to a patient
monitoring of at least one targeted gas (e.g. $CO_2$, $N_2$ or may be other gases capable of being detected, monitored, and measured) that is being expired or being expelled from an airway of a patient (e.g. an apnoeic or non-spontaneously breathing patient), and
determining a correlation between the delivered flow rate and said monitored gas signal, and
based on the correlation of the at least one targeted gas for a period of time, providing an indicator as to a determination as to airway patency.

It will be appreciated that alternatives described with respect to the first, second and third aspects described above are applicable to the sixth aspect.

According to the method and/or system and/or apparatus of this disclosure, the high flow therapy or flow therapy or respiratory support providing gases may comprise a substantial fraction (or a majority of the gases may be) $O_2$. This may be of particular importance given the condition of the patient, being non-spontaneously breathing or in an apnoeic condition. As such, it is beneficial to increase the amount of $O_2$ being provided or delivered to the patient to assist with oxygenation. Patient's with these conditions. The therapy gases provided may be as part of a high flow of gases comprising at least or greater than about 90% $O_2$.

It would be desirable to provide a system in which the humidity and temperature of the gas reach an ideal gas condition, for example, about 37° C. and about 44 mg/l as quickly as possible, and tubing for such systems.

For example, according to those various embodiments and configurations described herein, a flow rate of gases supplied or provided to an interface or via a system, such as through a breathing circuit, may comprise, but is not limited to, flows as defined by the high gas delivery flow rates described previously herein.

Such relatively high flow rates of gases may assist in providing the supplied gases into a patient's airway, or to different parts of a patient's airway. For example, such flow rates may allow for a delivery of such gases to the upper or lower airway regions. Upper airway region typically includes the nasal cavity, pharynx and larynx, while the lower airway region typically includes the trachea, primary bronchi and lungs.

Certain features, aspects and advantages of some configurations of the present disclosure have been described with reference to respiratory breathing circuits for use alongside or together with anaesthetic breathing circuits. However, certain features, aspects and advantages of the configurations as described may advantageously be used with other respiratory systems.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

Figure 2:
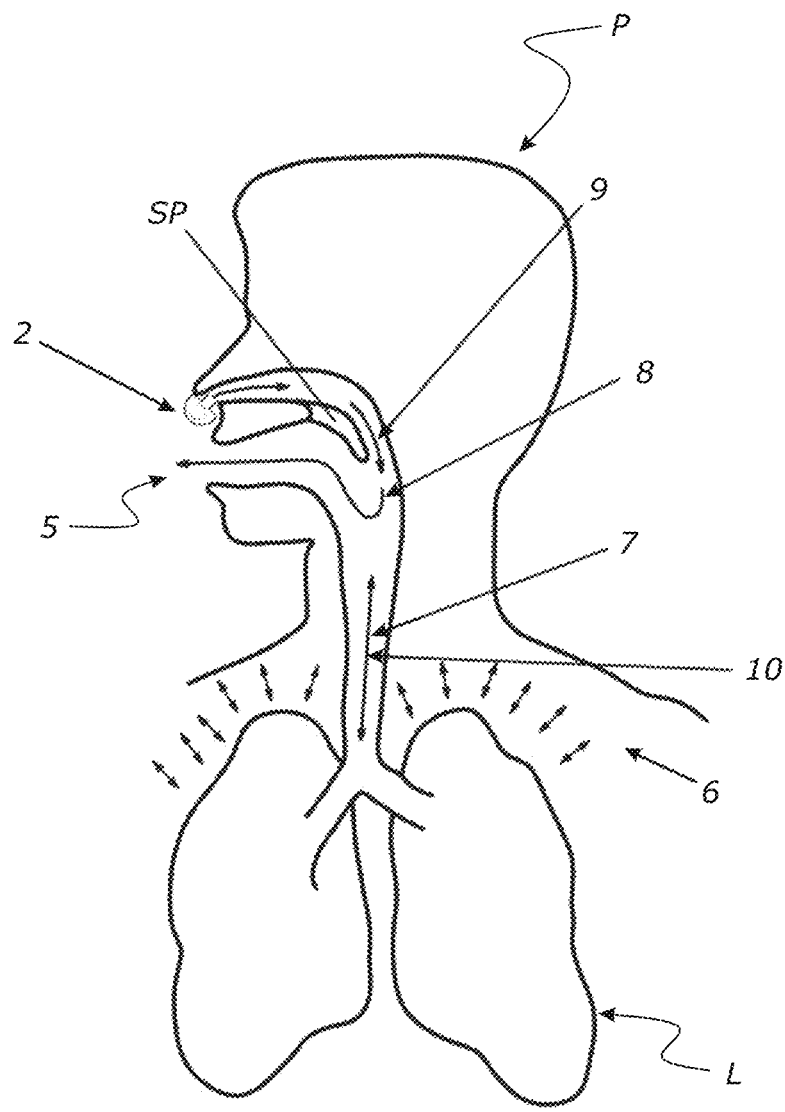
FIG. 2 illustrates a patient and different parts of their airway and parts of the airway which are referred to in the accompanying description.

FIG. 2 shows a typical airway of a person or patient, and includes arrows to indicate how a relatively high flow rate of gases supplied to that person or patient may be utilised to effectively push or drive the supplied gases further or deeper into a patient's airway than when the patient is under normal or typical self-driven respiratory conditions. The use of high flow rate gas delivery can help to push the gas flow and hence O2 deeper into the patient's airways. High flow rate of gases also helps flushing of the airways, and flushing of CO2 which also can help to push O2/respiratory gases deeper into the airways. In some situations, the high flow rate of gas delivery may be utilised when the patient is not spontaneously breathing, i.e. when the patient is apnoeic.

The method or system or apparatuses described herein may be used in respiratory care or therapy systems, in high flow therapy, or whether as a sealed or non-sealed interface, for example in-hospital respiratory care systems. The method or system or apparatuses may also be used to provide Nasal High Flow therapy. Particular application relates to the measurement or detection of certain gas or gases when expired or expelled from a patient's airway, and based on those measurements or detections, providing an indication of the patency of the patient's airway and/or an indication of the location of a possible occlusion or blockage or closure (or non-patency) of the patient's airway. As described below the described method or system or apparatuses are also useful for determining patency of an airway when a patient is already apnoeic or has reduced respiratory drive i.e. not breathing spontaneously. In these situations there is a need to detect if respiratory gases are reaching the lungs of the patient in contrast to trying to determine if the patient is breathing.

Figure 1:
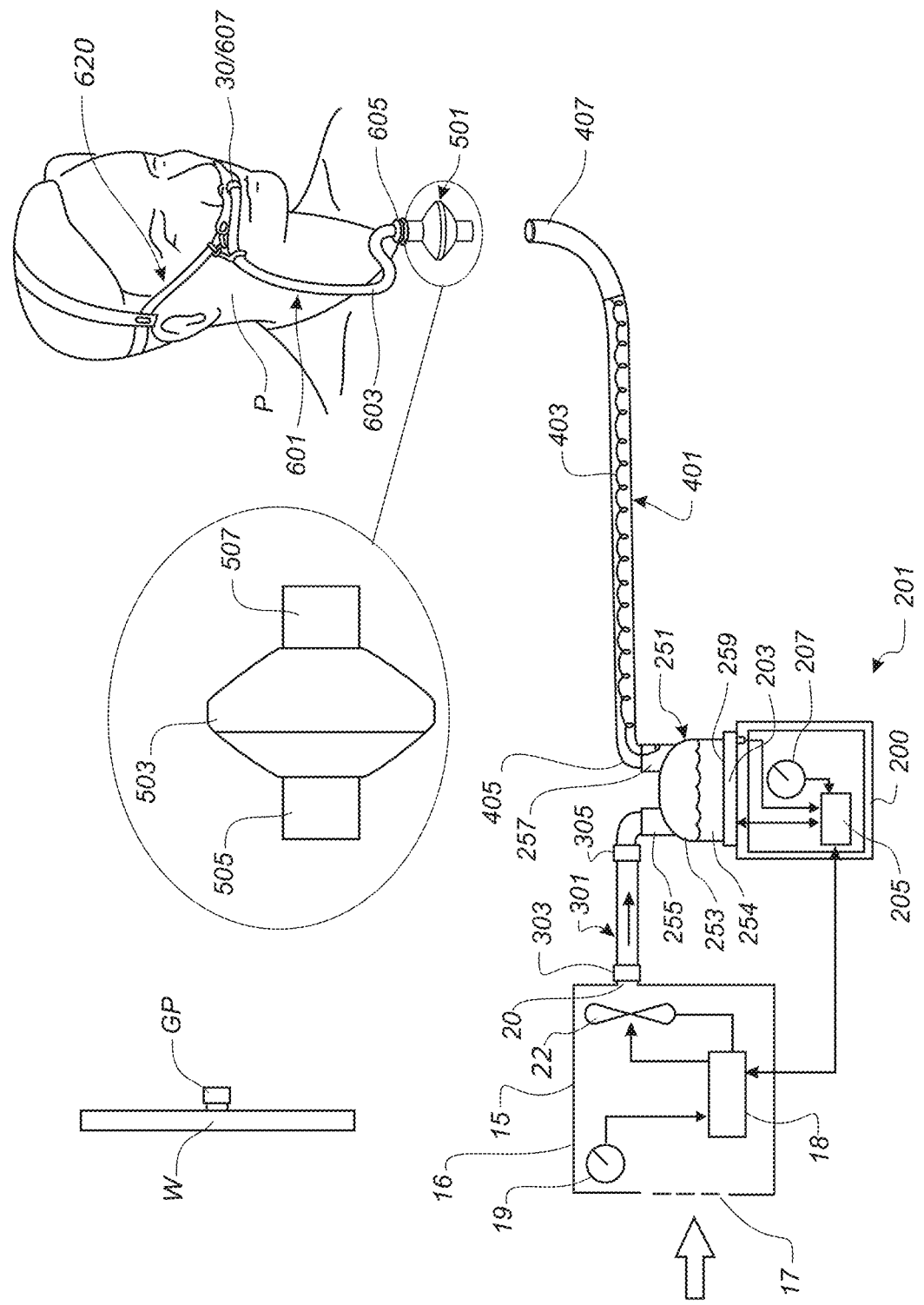
FIG. 1 shows a respiratory therapy support system comprising an example breathing circuit which may be combined with a patient interface to provide or delivery a desired flow therapy to a patient.

FIG. 1 illustrates a humidifying respiratory support system and a humidifying respiratory circuit. A patient P is receiving humidified and pressurised gases through a nasal cannula assembly of a patient interface 601 that is operatively connected to a humidified gases transportation pathway or inspiratory conduit 401 via a filter 501. The inspiratory conduit 401 in turn is connected to a humidifier 200 (including humidifier chamber 251) that is supplied with gases from a blower 15 or other appropriate gases supply means via a gases delivery conduit 301. The gases delivery conduit is a 'dry' conduit; that is, it is positioned upstream of the humidifier. Headgear 620 is provided to support and retain the patient interface against the patient's face. It will be appreciated the provision of a humidifier is optional, however there are patient airway benefits to provision of humidified gases so this may be a preferable inclusion. It will also be appreciated the provision of a filter is optional, however there are benefits to the provision of such an in-line filter (for example, the components of a circuit upstream of a filter may be used for providing a flow therapy or respiratory support to multiple patients, as there is reduced likelihood of upstream contamination of circuit components by components (provided downstream of the filter) by patients receiving a flow therapy or a respiratory support.

Where a humidifier is utilised, an inspiratory conduit 401 may be connected to the outlet 257 of the humidifier chamber 251 which contains a volume of liquid such as water. Humidifier chamber 251 may be formed from a plastics material and may have a highly heat conductive base 259 (for example an aluminium base) which is in direct contact with a heater plate 203 of humidifier 200.

The humidifier 200 may be provided with control means or electronic controller 205 which may comprise a microprocessor based controller executing computer software commands stored in associated memory. Gases flowing through the inspiratory conduit 401 are passed to the patient by way of the (optional) filter 501 and patient interface 601.

The controller 205 can receive input from sources such as user input means or dial 207 through which a user of the device may, for example, set a therapy mode. As part of this therapy mode the user of the device of the controller may automatically set a predetermined required value (pre-set value) of, gases flow rate, humidity or temperature of the gases supplied to patient P. In response to the user set therapy mode (or any other inputs) a user interface (such as dial 207, or a touch screen interface, or a button or buttons) and other possible inputs such as internal sensors that sense gases flow or temperature, or by parameters calculated in the controller, controller 205 can determine when (or to what level) to energise heater plate 203 to heat the water within humidifier chamber 251. As the volume of water within humidifier chamber 251 is heated, water vapour begins to fill the volume of the chamber above the water's surface and is passed out of the humidifier chamber 251 outlet port 257 with the flow of gases (for example air) provided from a gases supply means or blower 15 which enters the chamber through gases inlet port 255. It should be noted that it is possible to obtain the relationship between the humidity of the gases in humidifier chamber 251 and the temperature of the heater plate 203. Accordingly, it is possible to utilise the heater plate temperature in an algorithm or a look-up table to determine the humidity of the gases.

A blower 15 may be provided with a variable speed pump or fan 22 which draws air or other gases through the blower inlet 17. The speed of variable speed pump or fan 22 may be controlled by a further control means or electronic controller 18 (or alternatively the function of this controller 18 could be carried out by the other controller 205) in response to inputs from controller 205 and a user set predetermined required value (pre-set value) of pressure or fan speed or flow rate via dial 19 or other input device. Additionally, a touch screen or other input device or interface may be used to set the flow rate. Alternatively, the gases may be provided from a wall supply; i.e. a wall gas port GP in a wall W.

A housing 16 of the blower is provided with an outlet port 20. An inlet port 303 of the gases delivery conduit 301 and the outlet port 20 of the blower are provided with complementary coupling features to connect the outlet port 20 with the inlet port 303, and to provide a gases flow path therethrough. The complementary coupling features may in part be provided by an adapter insert (not shown), such an adapter insert providing for suitable connection features to allow conduits or other components to be connected or mated to the adapter insert and accordingly provided in a suitable pneumatic connection.

The system may also comprise (or be connectable to) a sampling device or apparatus comprising a sensor, such as a gas sensing head can be placed in the airway (for example the mouth/oropharyngeal region) of the patient. The sampling device may sense a parameter of the targeted or monitored gas. The sensed parameter of the targeted or monitored gas may be communicated to the controller of the system and used in the airway patency determination methodology described herein.

In some configurations the flow generator may be configured to provide an oscillating flow. The flow signal can comprise an oscillating flow signal to provide an oscillating flow. The flow signal may comprise one or more frequencies. The flow signal may comprise a base gas flow component and one or more oscillating gas flow components.

In some configurations the flow generator may comprise one or more valves in a manifold arrangement. Further the manifold arrangement may further comprises at least one proportional valve that is controlled by an associated controller 18. The valve can be used to deliver a desired flow rate or a desired flow signal. In some configurations the manifold comprises at least one pressure relief valves that are configured to open if the pressure in the manifold exceeds a max pressure.

In one example configuration the flow generator is controlled to deliver an oscillating flow that comprises oscillating flow components that are combined together to form a resultant oscillating flow. Each oscillating flow component may have a different frequency to the other components. Alternatively multiple oscillating flow components can exist.

In some configurations there are at least 3 oscillating components. The first component is at a frequency substantially similar to a resting heart beat of a human. The second component is a low frequency configured to provide for gas movement from the patients airways. The third frequency is a high frequency component. The three components are combined to create a resultant signal that is output from the flow generator (for example generated by the manifold).

By way of example the oscillating component can have a maximum flow rate of about 375 litres/min to about 0.5 litres/min (or about 270 litres/min to about 0.25 litres/min relative to the base component), or preferably of about 270 litres/min to about 15 litres/min (or about 120 litres/min to about 0.5 litres/min relative to the base component), or more preferably of about 150 litres/min to about 30 litres/min (or about 60 litres/min to about 10 litres/min relative to the base component). The oscillating component can have a minimum flow rate of about 370 litres/min to about 0.5 litres/min (or about 270 litres/min to about 0.25 litres/min relative to the base component), or preferably of about 240 litres/min to about 15 litres/min (or about 120 litres/min to about 5 litres/min relative to the base component), or more preferably of about 150 litres/min to about 30 litres/min (or about 60 litres/min to about 10 litres/min relative to the base component).

In some configurations the frequencies of the oscillating component may be varied based on one or more parameters sensed from one or more sensors such as O2 saturation, respiratory rate, respiratory phase, flow rate, $CO_2$ concentration, heart rate.

The varying gas flow with gas flow oscillations would be useful when a patients' respiratory drive is compromised or at least reduced, whether this is before, during or after a medical procedure or in any other situation. The varying gas flow with oscillating components predominantly assists to remove $CO_2$ from a respiring patient. $CO_2$ removal can be useful when a patient is apnoeic, or when a patient has diminished respiratory function, such as when sedated or descending into or coming out of anaesthesia. During these events, a patient's respiratory function might not be good enough to sufficiently clear $CO_2$ unassisted.

In some configurations, rather than using a blower 15, gases flow may be obtained from some other source(s) of gas. For example, in some configurations, source(s) of gas may comprise one or more containers of compressed air and/or another gas and one or more valve arrangements adapted to control the rate at which gases leave the one or more containers. As another example, in some configurations, gases may be obtained from an oxygen concentrator.

The system may also include a supplementary gases source to provide an air and supplementary gas mixture. For example, the supplementary gas might be O2. In some configurations, the apparatus may be adapted to deliver a high flow therapy. "High flow therapy" as used in this disclosure may refer to delivery of gases to a patient at a flow rate of greater than or equal to about 5 or 10 litres per minute (5 or 10 LPM).

In some configurations, 'high flow therapy' may refer to the delivery of gases to a patient at a flow rate of between about 5 or 10 LPM and about 150 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal real inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

The humidifier 200 can have a humidifier base comprising a housing 201 with the heater 203, the controller 205 that is coupled to the heater, and the user input device 207 to enable a user to turn on and off the humidifier and to select a desired temperature to be provided by the heater. The user input device 207 may for example be a button, switch, or touch screen display. The heater 203 may comprise one or more heating elements.

The humidifier base can be configured to receive the humidifier chamber 251. The humidifier chamber 251 comprises a housing 253 defining an internal liquid reservoir 254, an upstream gases inlet port 255 in fluid/pneumatic communication with the liquid reservoir, a downstream gases outlet port 257 in fluid/pneumatic communication with the liquid reservoir, and a base 259. The base 259 can be arranged to be positioned on or above the heater 203 to heat liquid in the liquid reservoir. The base may comprise a flange 261 that projects outwardly from an adjacent portion of the housing 253, to assist with locating the humidifier chamber in position on the humidifier base.

The gases inlet port 255, the liquid reservoir 254, and the gases outlet port 257 are in fluid/pneumatic communication to provide a gases flow path from the gases inlet port 255, through or past the liquid reservoir, to the gases outlet port 257 to heat and humidify gases travelling along the gases flow path.

The humidifier chamber 251 may be any suitable chamber that holds suitable liquid for use in humidifying gases, such as water for example. The humidifier chamber 251 may be a manual fill chamber, and may be filled through a liquid inlet port 263. Alternatively, the humidifier chamber 251 may be an automatically filling chamber, and liquid may be fed to the humidifier chamber from a liquid container, bag, or other liquid source. The humidifier chamber may comprise a float valve in the liquid reservoir, the float valve configured to control flow of liquid form the liquid container into the liquid reservoir.

A gases delivery conduit 301 may be located upstream of the humidifier chamber 251. Such a gases delivery conduit 301 may be in fluid/pneumatic communication with the humidifier chamber 251 or is configured to be placed in fluid/pneumatic communication with the humidifier chamber upstream of the humidifier chamber; i.e. with the humidifier chamber 251 downstream of the gases conduit 301. The gases delivery conduit 301 can be configured to receive one or more gases from a source of gas and deliver the gas(es) to the gases inlet port 255 of the humidifier chamber.

The gases delivery conduit 301 has an upstream gases inlet port 303 at one end of the conduit, and a downstream gases outlet port 305 at the opposite end of the conduit. The gases inlet port 303 and the gases outlet port 305 are in fluid/pneumatic communication to provide a gases flow path from the gases inlet port 303 through the gases delivery conduit to the gases outlet port 305. The gases outlet port 305 of the gases delivery conduit and the gases inlet port 255 of the humidifier chamber 251 may comprise complementary coupling features, to enable the gases delivery conduit 301 to be coupled to the humidifier to provide fluid/pneumatic communication between the gases delivery conduit 301 and the humidifier chamber 251. The complementary coupling features of the gases outlet port 305 of the gases delivery conduit 301 and the gases inlet port 255 of the humidifier chamber 251 may be disconnectable from each other to enable the gases delivery conduit 251 to be decoupled from the humidifier chamber 251. Alternatively, the complementary coupling features may be permanently or semi-permanently coupled.

In relation to the complementary coupling features, at least some of those may be provided by an adapter insert, such as adapter insert (not shown) comprising of suitable coupling feature(s).

The gases inlet port 303 of the gases delivery conduit may be provided with coupling feature(s) to enable the gases delivery conduit to be coupled to the source of gas.

An inspiratory conduit 401 extends from the humidifier chamber 251 to link the humidifier to a patient interface 601 via an in-line filter 501. The inspiratory conduit 401 may comprise a conduit heater 403 adapted to heat gases passing through the conduit 401. The heater 403 will help minimise or prevent the formation of condensation in the inspiratory conduit, which could otherwise occur due to a temperature differential between the interior of the conduit wall and exterior of the conduit wall. In other configurations the conduit heater 403 may not be present. The inspiratory conduit 401 comprises an upstream gases inlet port at one end of the conduit and a downstream gases outlet port 405 at the opposite end of the conduit, with the conduit defining a gases flow path from the gases inlet port 409 to the gases outlet port 405.

The humidifier chamber 251 is in fluid/pneumatic communication with the inspiratory conduit 401 upstream of the inspiratory conduit 401 or is configured to be placed in fluid/pneumatic communication with the inspiratory conduit 401 upstream of the inspiratory conduit; i.e. with the inspiratory conduit positioned downstream of the humidifier chamber 251. The gases outlet port 257 of the humidifier chamber 251 and the gases inlet port 409 of the inspiratory conduit 401 may comprise complementary coupling features, to enable the inspiratory conduit to be coupled to the humidifier to provide fluid/pneumatic communication between the humidifier chamber 251 and the inspiratory conduit 401. The complementary coupling features of the gases outlet port 257 of the humidifier chamber 251 and the gases inlet port 409 of the inspiratory conduit 401 may be disconnectable from each other to enable the inspiratory conduit 401 to be decoupled from the humidifier chamber 251. Alternatively, the complementary coupling features may be permanently or semi-permanently coupled. The humidifier outlet port 257 and the inlet port 255 may be standard medical taper connections such as ISO 22 mm medical taper connections. Alternatively other connections are contemplated such as proprietary connections on at least the outlet port 257 of the humidifier.

The inspiratory conduit 401 will typically have a longer length than the gases delivery conduit 301.

A filter 501 may for example be of any suitable type, but may comprise a generally cylindrical filter housing 503 with an enlarged central body portion. A leading edge of the enlarged central body portion comprises a tapering wall that terminates at an upstream gases inlet port 505, and a trailing edge of the enlarged central body portion terminates at a downstream gases outlet port 507. The gases inlet port 505 and gases outlet port 507 are in fluid/pneumatic communication via the central body portion. The filter may be a high-efficiency particulate arrestance (HEPA) filter. The enlarged central portion of the filter housing contains suitable filtration material. For example, the filtration material may comprise pleated paper, nano-fibers, or any other suitable filtration material, including sock filters, stacked disc filters, spiral filters, block(s) of filter material, a disc or discs of filter material with streams of filter material to free flow from or off the disc in fluid flow. The filter captures and prevents downstream passage therethrough of particulates, bacteria and/or other infectious material from the inspiratory conduit to the patient, and also captures and prevents upstream passage therethrough of bacteria and/or other infectious material from the patient to the inspiratory conduit.

The inspiratory conduit 401 can be in fluid/pneumatic communication with such a filter 501 upstream of the filter or is configured to be placed in fluid/pneumatic communication with the filter upstream of the filter; i.e. with the filter located downstream of the inspiratory conduit. The gases inlet port 505 of the filter 501 and the gases outlet port 405 of the inspiratory conduit 401 can comprise complementary coupling features, to enable the inspiratory conduit to be coupled to the filter to provide fluid/pneumatic communication between the inspiratory conduit and the filter. The complementary coupling features of the gases inlet port 505 of the filter and the gases outlet port 405 of the inspiratory conduit are disconnectable from each other to enable the inspiratory conduit 401 to be decoupled from the filter 501.

In one configuration, the complementary coupling features between the gases outlet port 405 of the inspiratory conduit 401 and the gases inlet port 505 of the filter comprise a 22 mm medical connection or 22 mm medical taper connection.

The filter 501, if utilised, can be in fluid/pneumatic communication with the patient interface 601 upstream of the patient interface or is configured to be placed in fluid/pneumatic communication with the patient interface 601 upstream of the patient interface 601; i.e. with the patient interface located downstream of the filter. In one configuration, the filter 501 is coupled to the patient interface 601 or is configured to be coupled to the patient interface 601.

The patient interface 601 may comprise a patient interface gases conduit 603 with an upstream gases inlet port 605 at one end of the conduit. The opposite downstream end of the patient interface gases conduit 603 is in fluid/pneumatic communication with a patient cannula 30/607 to deliver gases from the patient interface gases conduit 603 to a patient P.

In one configuration, the gases outlet port 507 of the filter 501 and the gases inlet port 605 of the patient interface gases conduit comprise complementary coupling features to enable the filter 501 to be coupled to the patient interface 601 to provide fluid/pneumatic communication between the filter and the patient interface gases conduit, with the filter in-line with a gases flow path through the patient interface gases conduit. The complementary coupling features may be disconnectable from each other to enable the filter to be decoupled from the patient interface gases tube of the patient interface. Alternatively, the complementary coupling features may be permanently or semi-permanently coupled.

The patient interface 601 is shown to be a nasal cannula, although it should be understood that in some configurations, other patient interfaces may be suitable. For example, in some configurations, the patient interface may comprise a sealing or non-sealing interface, and may comprise a nasal mask, an oral mask, an oro-nasal mask, a full face mask, a nasal pillows mask, a nasal cannula, a combination of the above or some other gas conveying system. It will be appreciated that other interfaces which extend at least partially into the airway of the patient may also be used as part of the envisaged system. In an embodiment, the patient interface 601 comprises a non-sealing interface such as a nasal cannula, which allows gases to be exchanged with the environment. For example, the non-sealing cannula allows carbon dioxide to be removed and/or cleared from the patient's airways while the patient receives flow therapy from the system. Further, in an embodiment, the patient interface is in the form of a nasal interface, such that the system does not interfere with other oral airway equipment and/or devices, for example, a tracheal tube in an intubation procedure. Accordingly, the patient may continue to receive flow therapy throughout the intubation procedure.

The patient interface gases conduit 603 forms a first gas lumen defined by a tubular wall. The first gas lumen is adapted to receive gases from the respiratory therapy system, via the inspiratory conduit 401 and filter 501 shown in FIG. 1, and channel the gases to the patient P.

As shown, in one example, the patient interface 601 can comprise two nasal delivery elements adapted to be positioned one in each of the patient's nares. Each nasal delivery element may be shaped or angled such that it extends inwardly towards a septum of the patient's nose. The gases inlet conduit 603 may comprise an unheated breathable tube that is configured to reduce the formation of condensate in the gases conduit 603.

Additionally, each nasal delivery element may be shaped or angled such that a tip of each nasal delivery element points, in use, towards a back of the head of the patient P.

In other embodiments, each nasal delivery elements can have different properties. For example, one of a pair of nasal delivery elements can be relatively long and the other nasal delivery element can be relatively short.

In some embodiments, a flow manifold may be configured to receive flow from two lateral sides of the flow manifold (e.g. from a 'left' and 'right' of the flow manifold when instead of just the 'left' or just the 'right' of a flow manifold, such as is for example shown in FIG. 1).

In some such embodiments, multiple gas lumens may be used to provide for pneumatic communication between a flow manifold and the respiratory therapy system.

In some embodiments, a flow manifold may be configured to receive flow from a non-lateral side of the flow manifold (e.g. from a 'bottom' or 'top' of the patient interface).

In other embodiments, a flow manifold may be a separately attachable component to be attached to the body of the patient interface, such as a nasal cannula or nasal mask. Such a manifold may be an entirely separate component able to be removed from attachment to the interface, or it may be de-attached or disconnected from an operational position to allow for a re-orientation of the manifold (and associated supply conduit) relative to the interface. For example, the manifold may be of a push-fit type arrangement to be push-fitted into a connection with the interface body, or may be of a swivel-type connection with the body of the interface allowing for a re-orientation of the manifold. A re-orientation allows for the supply conduit to be positioned to a left or a right side of the interface (and therefore changed from one side to another of the patient). This may allow for an improved convenience or arrangement of components in a system delivering gas to the patient. For example, if those assisting in a medical procedure need access to the patient from one particular side, then the manifold can be re-oriented and the supply tube re-positioned so as to extend from a different side of the patient. Such an arrangement allows for a relatively unobtrusive application of a patient interface and its associated components away from medical specialists.

The patient interface when in the form of a nasal cannula may utilise a headgear in the form of a strap that can be bifurcated (i.e. a line of weakness or other split arrangement can be configured) to allow for the headgear or a strap thereof to be reconfigured from a single strap arrangement into a bifurcated strap arrangement.

The patient interface when in the form of a nasal cannula may utilise a pair of side arms extending from the main body (to which the manifold is to be put into connection with). The side arms may comprise of features allowing for the retention or securement or positioning of a gas supply tube to the side arm (to prevent the gas supply tube from uncontrollably moving about).

The patient interface 601 may further comprise mounts and/or supports, e.g., cheek supports, for attaching and/or supporting the gas lumen 603 and/or cannula 30/607 on the patient's face. For example, a releasable connection system may be utilised to position or locate the interface upon the patent's face, yet allow for a relatively rapid removal or re-positioning of the interface if necessary.

Accordingly, an assembled patient interface when pneumatically coupled to a circuit may be used to deliver gases to a patient during pre-oxygenation, when the patient is being anaesthetized and/or when the patient has been anaesthetized (i.e. during the apnoeic window). For example, the apparatus may be used to deliver heated, humidified, high flow gas at between 5 l/min and 200 l/min, and advantageously at least at about 70 l/min, but may also be at least about 50 l/min, when a patient has been anaesthetized. When a patient has been anaesthetized, their respiratory drive is compromised and they are not breathing spontaneously. The high flow maintains the patient's oxygen levels at a safe level. This provides a useful alternative to a mask and bag that would typically be used to artificially ventilate a patient.

The system may include a wall source instead of a blower, or the blower may be a wall source.

The method may additionally or alternatively be used when the patient is being pre-oxygenated prior to being anaesthetized. At that time, the patient is breathing spontaneously. Pre-oxygenation is carried out to increase oxygen concentration in the patient's lungs.

In both instances the temperature of the gases delivered to the patient may advantageously be about 37° C. and the humidity may be about 44 mg/l $H_2O$.

A nasal cannula as the patient interface may provide a patient with a patient interface suitable for the delivery of high airflow, high humidity gas flow to the patient's nasal cavity.

A nasal cannula may be useful in the anaesthetic context or context of a patient who is apnoeic or non-spontaneously breathing, because the cannula has a relatively small footprint and is positioned on the upper lip, leaving the mouth and throat free for a surgeon or other medical professional to insert additional instruments with minimal obstruction or interference or to perform procedures on the mouth/throat with minimal obstruction or interference.

In some embodiments however patient interface may be of the type comprising a sealing or non-sealing interface, and may further comprise a nasal mask, an oral mask, an oro-nasal mask, a full face mask, a nasal pillows mask, a nasal cannula, a combination of the above or some other gas conveying patient interface system In one form of a nasal cannula assembly 30/607 there may be provided a face mount part including a pair of tubular nasal prongs integrally molded with or removably attached to the face mount part, and a gases flow manifold part that is integrally molded with or attached to tubing 603, such as that described above.

As described above, a nasal cannula can be provided with a removably attachable manifold for delivering the flow of gas to the interface, the manifold able to be re-oriented so as to have a gas supply connection put to either a left or a right side of the interface (or the patient). One or pair of side arms or cheek support of such a nasal cannula allow for the positioning of the interface on a patient's face and may optionally include a relatively soft outer material or overmoulded material in at least the patient contacting surfaces. In one embodiment the cheek supports are rigid, and they may also be overmoulded by a relativity softer material such as silicone or TPE.

The removable manifold may be re-oriented as previously described. Such a re-orientation can be manually done by a user or a person assisting the patient/user.

A headgear as disclosed herein may be provided in combination with the nasal cannula and may include at least one strap of which is bifurcatable (i.e. may have a line of weakness or other pre-defined zone allowing a user to separate the strap into two parts).

The body of the nasal cannula may include a barrel shaped portion into which the manifold is inserted and can be removed therefrom to allow for side swapping. The nasal cannula may additionally or optionally include headgear connectors that connect to one or both side arms.

The face mount part and prongs may be moulded from silicone or other flexible material as is known is the art of cannula construction. The gases flow manifold part may be made from a hard plastics material, although it may be manufactured in other suitable materials.

The face mount part may be integrally molded with the prongs and may be shaped to generally follow the contours of a patient's face around the upper lip area.

The gases flow manifold part may be generally tubular in shape having a substantially circular inlet (not shown) on one side that curves around to an elongated oval outlet. The circular inlet receives the end of the conduit or tubing 603, so that gases are supplied to the gases flow manifold part and are able to flow through the inlet and out the outlet. The tubing 603 may be permanently fixed to the manifold part, or may be releasably attachable.

The outlet, being elongated and oval in shape, can fit into an elongated recess in a friction or snap fit engagement with the manifold, such that a substantial force is required to remove the manifold part from such an elongated recess. Further, as the face mount part may be flexible and the manifold part may be made from a harder plastics material it is possible for the manifold part outlet to be relatively more easily pushed or forced into such an elongated recess. When the manifold part is engaged with the face mount part and in use, gases flow from the tubing 603, through the gases flow manifold part out its outlet 29, into each of the oval recesses into each of the prongs and into the patient's nares.

The face mount part elongate recess and manifold part outlet may be symmetrical in shape and configuration and therefore the manifold part can be capable of being switched or flipped such that the tubing 603 extends from either the left or right side of the patient's nares. This means that the nasal cannula assembly and associated tubing 603 are relatively unobtrusive as the cannula 20 only requires a single horizontal side entry, not two entries.

Such a generally described nasal cannula assembly may be more comfortable to wear as it sits under the septum of the nose and supports the two nasal prongs. As the prongs are made in one moulding of a soft material such as silicone the prongs are easy to insert in the patient's nares and comfortable to the patient.

The gas used in the embodiments described herein in relation to delivery or provision of a flow therapy or respiratory support will typically be oxygen. Alternatively, the gas could be air or other suitable gas(es), or mixes of air with supplemental oxygen or other gases suitable for the patient.

The liquid used in the configurations described above for humidification will typically be water. Alternatively the liquid could be other liquid(s) suitable for a humidification process.

More specifically, in relation to some surgical procedures, it is desirable to have unobstructed access to elements of the patient airway—for example the vocal chords, the glottis, or the trachea—while the patient is anaesthetised and their respiratory system is paralysed.

For those paralysed patients, an endotracheal tube would normally be used to secure the airway and provide a pathway for the application of artificial ventilation, but the use of an endotracheal tube may be undesirable in these situations as the tube not only completely blocks the lower airway but also significantly obstructs access to airway elements above the inflated cuff of such an endotracheal tube arrangement. Similarly, a laryngeal mask also substantially obstructs access to the airway and therefore is not typically suitable for use during this type of procedure.

Until recently, medical practitioners or clinicians may have used various forms of jet ventilation using oxygen supplied via a narrow catheter introduced into the trachea via the mouth (for example, a Hunsaker catheter) to provide a degree of ventilation and gas exchange. However, the catheter must still be supplied via a tube which runs down the airway and, although obstruction is less, access is still restricted. Clinicians must also be aware of the potential fire and damage risks of introducing a plastic tube down the airway in an oxygenated atmosphere when certain operations such as laser ablation or cauterisation may be carried out.

A high flow of gases (such as O2 or oxygenated gases) or high flow gases therapy or respiratory support provided via a patient's nares (e.g. a nasal interface) provides the ability for ventilation of paralysed patients using high flows of humidified oxygen or gases, for example supplied via a nasal cannula or other forms of patient interface. The supplied gases (e.g. which include oxygen) can enters the nose via the patient interface (e.g. via nasal prongs of a nasal cannula) and flows out of the mouth, causing substantial turbulent flushing of the pharyngeal space as it does so. Such gas flows can be optionally humidified. Such a high flow creates a relatively small positive pressure in the trachea and lungs which effectively splints the airway and alveoli open—partially mitigating against atelectasis. As oxygen is consumed in the alveoli, fresh gas is naturally drawn down the trachea to make up that absorbed across the alveolar membrane.

Simultaneously, carbon dioxide is produced by the body and transported to the lungs via the bloodstream. It accumulates in the alveoli, and diffuses to the bronchi.

As the heart beats, it causes periodic variations of pressure in the arterial system, and these pressure variations are transmitted to the lungs via the arteries which surround them. In addition, the heart is in partial contact with the lungs and this also gives rise to periodic pressure variation applied to the lungs tissue. The pressure variations applied to the lungs cause small periodic lung volume variations which—in the paralysed or non-spontaneously breathing patient—periodically squeeze gas accumulating in the bronchi up the trachea towards the pharynx (when the heart is causing net compression of the lungs) and periodically suck gas from the pharynx down towards the lungs (on the other half of the heart cycle when the net compressive force is released).

The periodic flow in the trachea caused by the action of the heart is commonly termed: 'cardiogenic oscillation'. For most patients, the volume displaced by the action of the heart is sufficient to transport a small amount of gas (that includes CO2) from the lungs to the pharynx on the expiratory part of each cardiogenic cycle, and then to bring gas (that includes O2) back from the pharynx to the lungs on the inspiratory part of the cycle.

When gas comprising CO2 reaches the pharynx on the expiratory part of the cardiogenic cycle, the gas is almost immediately swept out of the mouth by the relatively high flow of gas being provided by the patient interface (e.g. from the nasal cannula) that is providing the flow therapy or respiratory support.

Similarly, the inspiratory part of the cardiogenic cycle causes substantially enhanced transport of gas that comprises oxygen from the pharynx towards the lungs—adding to the flow resulting from the net consumption of oxygen in the alveoli.

It is worth noting that if there is no flow from the patient interface (e.g. nasal cannula), cardiogenic action on its own may not be sufficiently high in amplitude to transport significant amounts of gas comprising CO2 from the lungs, through the tracheal and pharyngeal deadspaces, and out of the patient's airway (such as their mouth). Sufficient gas comprising CO2 clearance may only occur if the pharyngeal dead space is flushed.

In various examples, for example with high nasal gas flow rates, the cardiogenic oscillations therefore act as a pump, transporting gas from the lungs to the flushed pharynx, and enhancing the transport of gas back from the pharynx to the lungs. This is illustrated in FIG. 2.

FIG. 2 illustrates an apnoeic ventilation system via cardiogenic action. Shown is a patient P with a flow of gas as a flow therapy or respiratory support being provided or delivered to a nare or nares of the patient's nose via a patient interface 2. The provided or delivered gas entering the nasal passages and the patient's airways. Gas can be transported down the upper airway into the patient's lower airway toward the lungs L. The lungs L can have some oscillating pressure on them caused by pulsatile blow flow from the heart, helping to cause cardiogenic action, indicated by arrows 6. Gas flow can be expired or expelled (or exhausted) from the patient's mouth 5.

Although a constant flow rate of the flow therapy or respiratory support may be provided or delivered to the patient, oscillations may be imposed upon that flow. An oscillating flow of gas in the patient's trachea may be resultant from the cardiogenic action of the patient's heart beat. The relatively high flow rate of flow therapy or respiratory support provided or delivered to the patient via the nose can assist in flushing gas which is expelled or expired from the patient's lungs in response to this oscillating flow of gas in the trachea. The gas and flushing can be exhausted out through the patient's mouth or oral cavity when subjected to flow therapy or respiratory support delivered via the nose. Application of an oscillating flow rate is described in more detail below.

For apnoeic ventilation to operate effectively, it is important that a patent airway exists between the lungs and the pharynx. An occlusion or blockage in the trachea or vocal chords will interrupt the action of the cardiogenic pump action, preventing both the ability to provide flow therapy or respiratory support (including oxygenation) to the patient, as well as preventing clearance of gas being expired or expelled from the patient, e.g. CO2 clearance or flushing action.

Accordingly, there are particular benefits to clinicians (as well as for patient safety and health) if the patency of a patient's airway could be monitored and/or determined more effectively.

It is also important that gas flow can travel unobstructed from the patient interface providing flow therapy or respiratory support (e.g. nasal cannula) at the nose, through the oropharynx, and out of the mouth. If this flow passage is blocked or occluded or otherwise obstructed, the pharynx will not be adequately flushed and CO2 can build up in the alveoli and trachea, displacing oxygen and eventually leading to both a fall in O2 saturation in the blood and hypercapnia.

Sensing Targeted Gas (e.g. CO2) Concentration Variations in the Pharynx/Mouth

The lungs continuously produce CO2 which then is expired or expelled via the trachea and mouth in a series of pulses, by the cardiogenic action in a non-spontaneously breathing patient or an apnoeic patient.

By monitoring the variation of CO2 concentration with time in the pharynx/mouth it is therefore possible to check if CO2 is being driven up the trachea from the lungs, and also if it is being swept away by the relatively high flow of flow therapy or respiratory support (e.g. gases which may comprises of oxygen) being provided or delivered, for example via the patient's nose from a nasal patient interface (e.g. nasal cannula).

Figure 3:
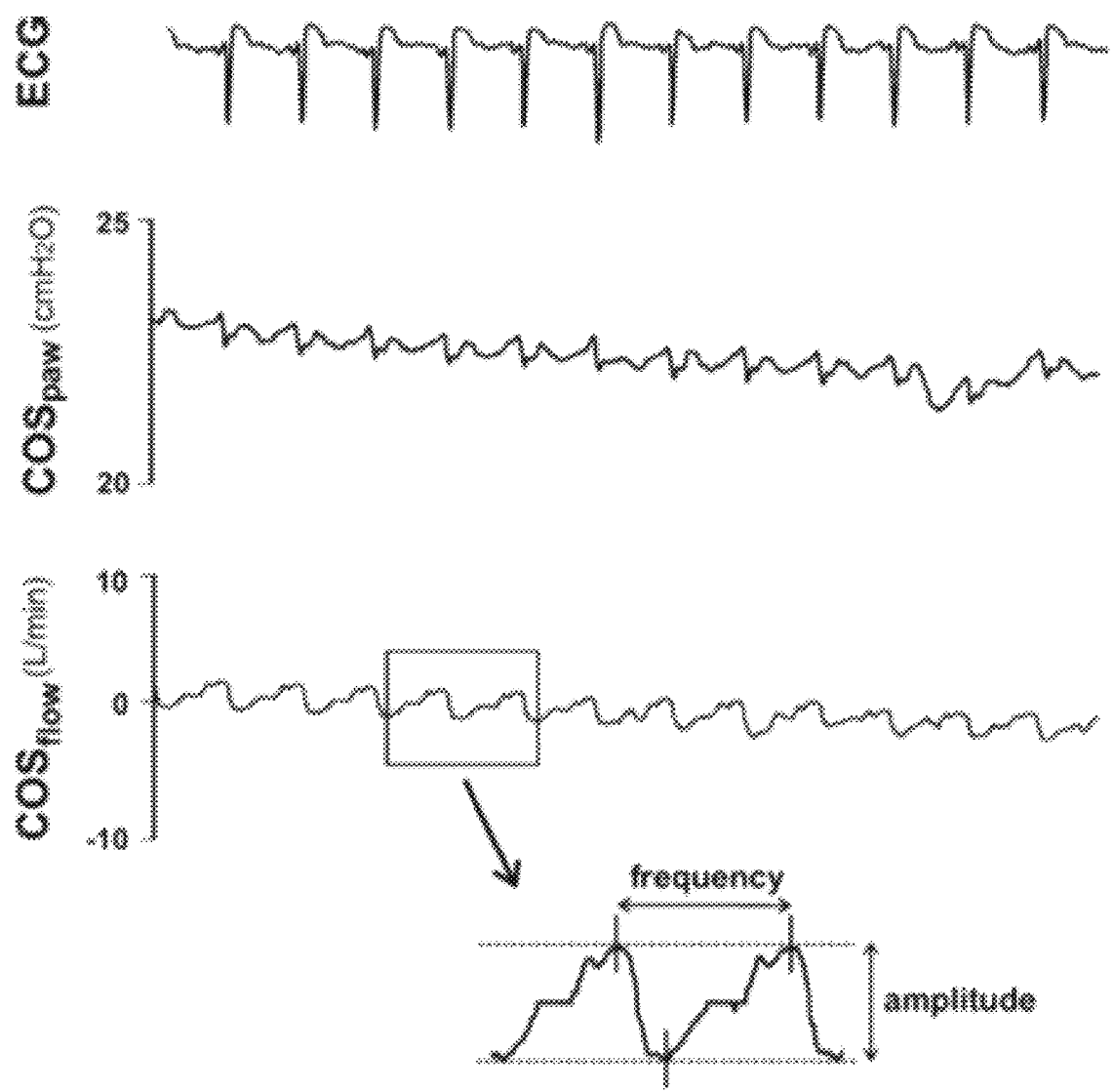
FIG. 3 is an example of a cardiogenic oscillation (COS) during an inspiratory phase for a patient, where the COS is synchronous with the cardia cycle (ECG).

Volume of Targeted Gas (e.g. CO2) Cleared Per Cardiogenic Cycle in Apnoeic Ventilation and Concentration at the Mouth FIG. 3 is a plot of flow out of the mouth caused by cardiogenic oscillation. Cardiogenic flow volume over the expiratory part of the cardiogenic cycle varies from person to person, but is typically in the range 20-60 ml.

In one example, model experiments indicate that approximately 5-30 ml of gas exchange per cycles is achievable between the lungs and pharynx for cardiogenic flow volumes in this range. Assuming that the partial pressure of CO2 in the lungs is about 40 mmHg, the cardiogenic pump may therefore clear about 0.27-1.59 ml of CO2 into the pharynx per cardiogenic cycle. As illustrated, the cardiogenic oscillations of gas flow can be mapped to the heart beat of the patient.

Gas cleared from the lungs can be mixed with the relatively high flow of gas passing through the pharynx (provided or delivered as a flow therapy or respiratory support), and this causes substantial dilution of the CO2 (and other gases being expired or expelled at the same time).

In one example, if the flow of oxygen through the pharynx is 70 l/min, and the expiratory part of the cardiogenic cycle lasts for 0.4 seconds, the concentration of CO2 exiting the mouth during each cardiogenic pulse will be approximately 570-3405 ppm (0.057-0.34%, corresponding to a partial pressure of 0.43-2.58 mmHg).

In order to monitor the pulse of CO2 exiting the mouth (or travelling through the pharynx) during a cardiogenic expiration, it is desirable to have a gas sensor which is capable of measuring concentrations which are roughly one tenth of these values so that the concentration pulse waveform can be tracked. This corresponds to a sensitivity of approximately 57-340 ppm or 0.04-0.26 mmHg, with a time response of 0.2 seconds or less.

The implementation and use of high-sensitivity CO2 sensing technology into the method and system and apparatuses disclosed herein would allow for the monitoring of the concentration variation of CO2 in the pharyngeal flow resulting from cardiogenic pumping of CO2 from the lungs.

Alternative to Capnography of Targeted Gas (e.g. CO2) Cleared by Cardiogenic Action for Assessing Airway Patency in Apnoeic Ventilation In a further example, the concentration of CO2 in the lungs is relatively small—roughly 5% at an arterial CO2 level of 40 mmHg. This low concentration of CO2 is further substantially reduced when the CO2 pumped up from the lungs is diluted with the high flushing flow of the flow therapy or respiratory support being delivered or provided to the patent, for example in the pharynx—and this contributes to challenges of being able to effectively an accurately measure the concentration of gases being expired or expelled from the patient challenge described above.

Due to such challenges, when under apnoeic ventilation, a patent can be supplied with high concentrations of oxygen (not limited to, but may include 100% oxygen). As such, it is possible to effectively flood the lungs with high concentrations of a benign tracer gas (being a targeted gas which is to be subsequently detected and measured) for short periods and to then monitor the cardiogenic pumping of a targeted gas from the patient's lung system. This allows for an effective monitoring of the patient's airway patency.

Under normal spontaneous breathing conditions, the patient would breathe air which is a mixture of approximately 80% nitrogen and 20% oxygen. In light of this, the method or system or apparatus as disclosed herein facilitates for the ability to briefly flood the lungs of a substantially (or fully) oxygenated apnoeically-ventilated patient with a 50:50 nitrogen/oxygen mixture (or other mixtures of gases, containing a gas which is to be targeted, detected and measured), and then subsequently allowing clearance of the nitrogen (or other targeted gas) to take place by cardiogenic action. Such an approach would place the patient at only small extra risk of desaturation, yet would provide a significant benefit by allowing a clinician to be provided with information relating to the monitoring of the targeted gas, such as nitrogen, and it's clearance at relatively higher concentrations.

Therefore, in one particular embodiment of the disclosure herein, there is provided a flooding of the patient's lungs with a mixture of gas (such as nitrogen/oxygen mix) to allow for monitoring of airway patency. A particular procedure may be provided as follows:

1. Ensure the patient is substantially oxygenated (or at least their oxygenation saturation levels are increased) (optionally, an oxygen saturation of greater than about 98% may be achieved) using a relatively high flow of gas (provided via a nasal interface), the flow of gas comprising oxygen (optionally humidified oxygen). The flow of gas may be of at least 70 l/min, and about 1 cmH2O pharyngeal splinting pressure.

2. Remove or substantially reduce the flow of gas from step for a relatively short period (e.g. remove or reduce the humidified oxygen supply for about 1-2 seconds). This removes or reduces the effective airway splinting pressure and allows the lungs to deflate slightly.

3. Apply a gas comprising a targeted gas (e.g. may be humidified nitrogen/oxygen mix) at a flow rate (e.g. may be a relatively high flow according to the flow rates of a flow therapy or respiratory support needed for the particular patient, and may for example be about 70 l/min or greater), for a period of time (e.g. may be for about 1-3 seconds). The flow of gas provided during step 3 here can at least partially reinflate the lungs, but the lungs are at least partially reinflated using with the gas comprising the targeted gas (e.g. now with nitrogen/oxygen mix), thereby ensuring that the gas comprising the targeted gas reaches the lungs.

4. Restore the flow therapy or respiratory support provided from step 1 (e.g. a humidified oxygen supply), without allowing a reduction in the pressure applied to the patient's airways, so as to prevent the lungs from deflating.

5. Monitoring the variation of concentration of the targeted gas (e.g. nitrogen) in the mouth/pharynx with time, as it is pumped out of the lungs by cardiogenic action and swept out of the mouth by the flow of gas provided by the flow therapy or respiratory support (e.g. the relatively high flow of humidified oxygen).

If a 50:50 nitrogen/oxygen mixture is used in step (3) above, the concentration of nitrogen will initially be roughly 10 times the concentration of CO2, potentially providing substantial advantage in monitoring the clearance. It will be appreciated that alternative mixtures of gas can be utilised for this procedure, with different gas being used at the targeted gas to be detected, measured and monitored.

Note that if the deflation/inflation procedure is not carried out, and instead a high flow of oxygen was simply replaced with a high flow of a gas mix, such as a nitrogen/oxygen mix, it would not be possible to ensure that the physiological dead space becomes full of the gas mix (e.g. the nitrogen/oxygen mixture) or that the targeted gas (e.g. nitrogen) reaches the lungs.

Monitoring Airway Pressure to Ensure Sufficient Flow for Splinting and Mitigation of Atelectasis A relatively high flow of gases provided to a patient, such as by a flow therapy or respiratory support (e.g. the gas may be oxygenated or contain supplemental oxygen to elevate oxygen concentration above that of air sole), for example via the patient's nose, can help in creating or provision of a small splinting pressure in the patient's airway (not limited to, but may be about 0.5-5 cmH2O). Although relatively small, this pressure can helps inflate alveoli and assist in mitigating against atelectasis. This extra pressure may be particularly important in obese patients or other patients who are susceptible to atelectasis.

If the pharyngeal airway from the nose is partially blocked, the splinting pressure may be substantially reduced thereby putting patients at increased risk of one or more of: airway collapse, atelectasis, desaturation.

Therefore, the method or system and apparatus as disclosed herein optionally also provide for the monitoring of the splinting pressure in the airway by a pressure sensor or probe which can be placed just above the larynx. This can provide additional information to enable a clinician further assess the patency of the pharyngeal airway, or the signal or output of pressure data from such a sensor or probe can contribute to a determination of a patient's airway patency.

Figure 4:
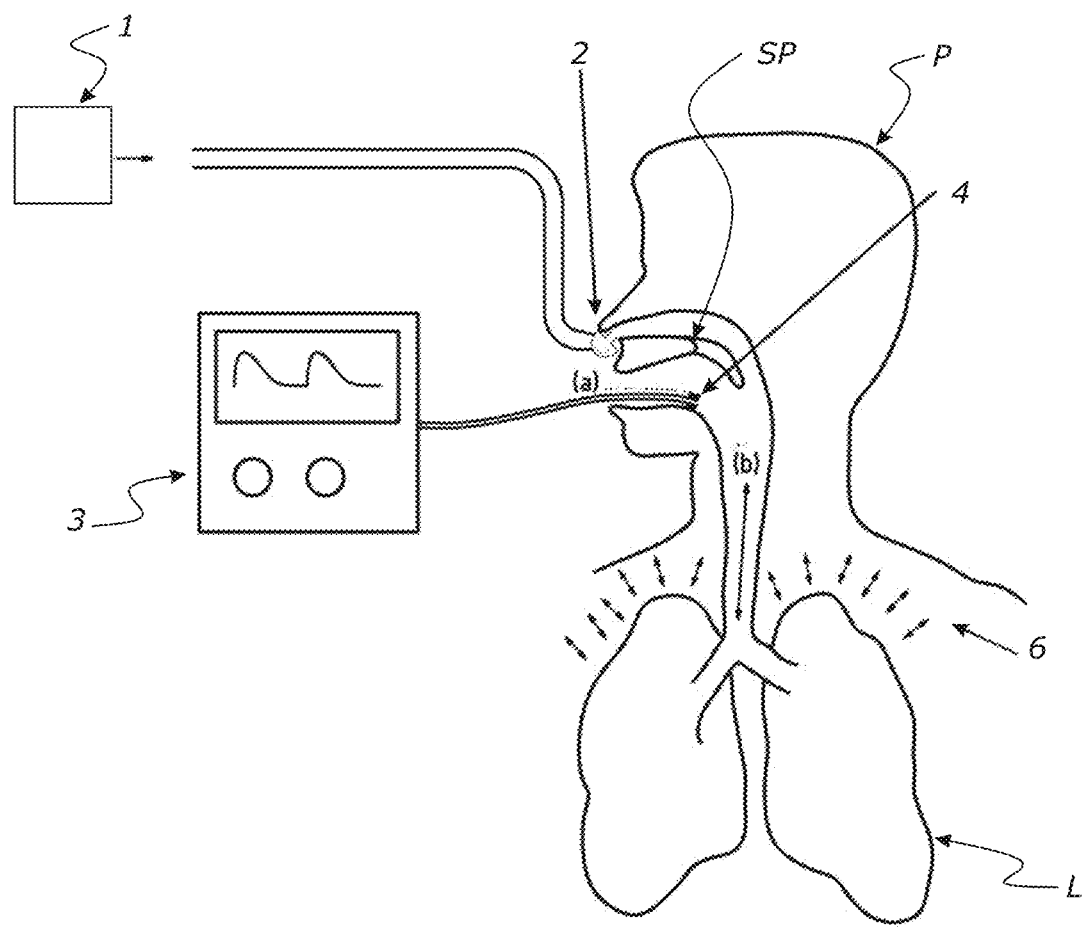
FIG. 4 shows components of a system for implementing the method as disclosed herein utilising a gas source and a nasal patient interface and a sensor in the form of a gas analysing sensor.

Sensing Targeted Gas (e.g. CO2) Concentration Variations in the Pharynx/Mouth to Assess Airway Patency FIG. 4 illustrates an example of a system for assessing airway patency by monitoring a targeted gas, such as CO2, which is expired or expelled from the lungs of a patient P by cardiogenic action.

The anaesthetized and/or paralyzed respiratory system of a patient is apnoeically ventilated by providing or delivery a flow therapy of respiratory support, for example using a relatively high flow of gases (e.g. humidified oxygen) supplied via a nasal patient interface (for example a nasal cannula). The delivered or provided flow rate of the gases is sufficiently high enough to achieve at least some splinting pressure to mitigate against atelectasis and ensure sufficient absorptive capacity of supplied gases (e.g. oxygen) by the lungs so as to try and avoid a desaturation situation.

Precautions can be implemented to avoid or reduce the chances of patient barotrauma (for example a pop-off valve or other pressure relief valves or vents may be to release or relieve pressure in the circuit or the patient interface providing the flow therapy or respiratory support).

As shown in FIG. 4, the patient's mouth is open so that a flow therapy or respiratory support of a flow of gases being provided or delivered via the nose can travel through the pharynx and exit via the mouth.

A sampling device or apparatus comprising a sensor, such as a gas sensing head can be placed in the mouth/oropharyngeal region of the patient. The positioning of the sensor can be placed along the base of the mouth/oropharynx anywhere between the positions (a) and (b) as shown in the FIG. 4.

The sampling device or apparatus may be a separate device or may be integrated with the nasal cannula or removably coupleable to the nasal cannula.

Position (a) is shown as being at or near the base of the mouth entrance, between the teeth and position (b) is shown as being at or near the entrance to the trachea. The sensor head should not be placed in the valleculae as this presents a risk of blocking gas flow into the sensor and is also then not located so as to be more directly in the gas stream coming from the trachea. The range of different positions for locating the sensor provides the clinician with flexibility to then avoid obstructing the surgery site depending on the procedure to be carried out. The range of positions is possible because the patient is apnoeic and there is a reduced chance of irritation or discomfort for the patient.

In some configurations gases may be sampled from both the mouth and nose of a patient.

Alternatively or additionally, the sampling device/apparatus may include a sampling tip. The tip may be designed to maximize $CO_2$ collection and prevent/reduce introduction of saliva into the sampling device/apparatus. The sampling device/apparatus may include a hollow tube that is coupled to the gas sensor that is disposed remote to the patient e.g. in the flow generator. The sampling tip may be a malleable tip that can hold its position when manipulated into an operable position.

The sensor can be connected to a sensitive side stream gas (e.g. $CO_2$, $N_2$, helium) sensor which aspirates a sample of gas from the mouth/oropharyngeal region at a relatively low flow rate. The flow rate aspirated into the sensor should be less than about 200 ml/minute (one fifth of the peak anticipated cardiogenically-induced gas flow in the trachea).

If necessary, precautions can be taken to avoid aspiration of fluids and water vapour into the sensor, such as for example using a water trap or a filter in conjunction with semi-permeable tubing (for example such as a material referred to as NAFION). These are not shown in the figures. In the context of the above embodiment the sampling tip can be shaped or include wall arrangement for example castellation to prevent fluids being aspirated.

The sensor (e.g. a gas analyser type sensor) can provide for a signal or output which can be processed by a processing unit or controller, and a corrected or compensated output or signal of a detected and measured targeted gas concentration can be provided via an output (e.g. a GUI) or other information display. Alarms or other warnings may be issued or raised depending on the variation in concentration of the targeted gas measured over time.

Similarly, an input of the patient's heart beat or cardiogenic activity may be correlated or related to the sensed targeted gas concentration so as to provide an output of information for a clinician.

Similarly, an input of the flow rate of gases provided or delivered to the patient (i.e. the flow rate of the flow therapy or respiratory support provided to the patient) may be sensed or measured by a flow meter device, and such an input provided for a correlation or related to the sensed targeted gas concentration so as to provide an output of information for a clinician.

As described above the flow of gases may be provided or delivered with an oscillating flow to the patient or superimposed oscillations of a positive gas flow to a patient may be delivered. The flow may help improve or accentuate gas exchange from the patient's airway. The flow may additionally or alternatively help improve or accentuate gas exchange due to cardiogenic pulses occurring within the patient.

The flow may be the sum of atone or more oscillating waveforms. The oscillating flow or each oscillating waveform may be substantially sinusoidal (i.e. generated based on the Sine function). In one embodiment the flow is the sum of two or three oscillating waveforms. In one embodiment the flow may comprise an oscillating waveform with the same frequency characteristics as a patient's heartbeat or cardiogenic pulsing.

The flow of gases may be delivered in accordance with a flow signal. The flow signal (and hence the delivered) may has one or more of the following signal characteristics or parameters: a frequency, an amplitude, a wave shape, or wave form and/or a phase. The frequency may be substantially repeating over a period of time. Further, the wave shape or wave form may be substantially repeating over a period of time.

The parameters of the flow may be selected to optimize or increase the expiration or expulsion of said gas from said patient. The oscillating flow may have a frequency component or components to improve gases expulsion due to the cardiogenic mechanism. Alternatively, or additionally a parameter of the flow may be selected (for example the amplitude or period of the oscillations) to maximize expulsion of target gases.

The terms targeted gas and monitored gas may be used interchangeably. The signal measured by a sensor in the system may be a targeted gas signal or a monitored gas signal respectively.

The flow of gases delivered to the patient may accentuate and/or facilitate the expiration or expulsion of at least one targeted gas. In this way the measurements of the at least one targeted or monitored gas may vary in response to the flow delivered to if the patients airway is unobstructed or patent over a period of time.

A correlation can be determined between the delivered flow rate and measurements of the at least one targeted or monitored gas as a monitored gas signal, and the indication of airway patency of the patient can be based on this correlation.

The monitored gas or targeted gas, may be: $CO_2$ or $O_2$, or a gas indicative of the concentration of carbon dioxide or $O_2$. Additionally, the monitored gas may be any of the targeted gases described above.

In an embodiment the target gas is $CO_2$. As $CO_2$ is expelled from the lungs. As such $CO_2$ provides a good indication of airway patency especially, when 100% $O_2$ is being delivered to a patient that is not spontaneously breathing or has very low respiratory drive.

The physiology of how the correlation allows for determination of airway patency is described below with respect to a nasal cannula interface and an oscillating flow rate, however it in envisaged that other interfaces (and indeed flow rate profiles varying or otherwise) could be utilised. When flow is applied (for example by via a flow generator comprising a proportional valve as described above) through a nasal cannula and the upper airway of the patient is patent, a substantial portion of the flow passes down the nasopharyngeal passage and exits through the mouth. In a normal adult when a flow rate of 70 l/min (or up to 100 l/min when the patient is apnoeic, or with diminished respiratory drive) is applied through the cannula, the pressure generated in the pharynx is typically between 0.5-5 cm.

If, in addition to the upper airway, the lower airway (larynx/trachea etc.) is patent, this flow or pressure is transmitted to the lungs. An increase or decrease in the oscillating flow rate provided will result in a corresponding increase or decrease of the pressure in the pharynx (at a rate approximately proportional to the square of the flow rate). Because the lungs of a patient are generally compliant they will expand when pressure is applied to the airway. Consequently, when the flow applied through the interface is increased, the increase in pressure created in the airway causes the lungs to expand and at least some of the flow rate of gas passes down the airway from the pharynx into the lungs. Conversely, when the flow applied through the cannula is decreased, the pressure in the airway falls. The lungs then contract and some of the gas in them is forced up the trachea to enter the turbulent flow in the pharynx from where it is mixed with the gas stream ejected through the mouth. Further, CO2 is also produced as part of cardiogenic pulsing (as described above) and will be a component of the gas forced up the trachea.

If gas exchange is occurring in the lungs (for example either by cardiogenic pulsing or normal gas exchange) the lungs will contain CO2, when the gas is forced up the trachea (i.e. by a decrease in applied flow rate), this will be manifest as a transient rise in CO2 concentration in the gas leaving the mouth as the flow applied to the cannula falls. This transient increase in CO2 concentration will only be seen if both the upper and lower airways are patent (i.e. flow is able to get from the nose to the pharynx to pressurise it, and gas is able to pass up and down the trachea between the lungs and the pharynx).

Figure 12:
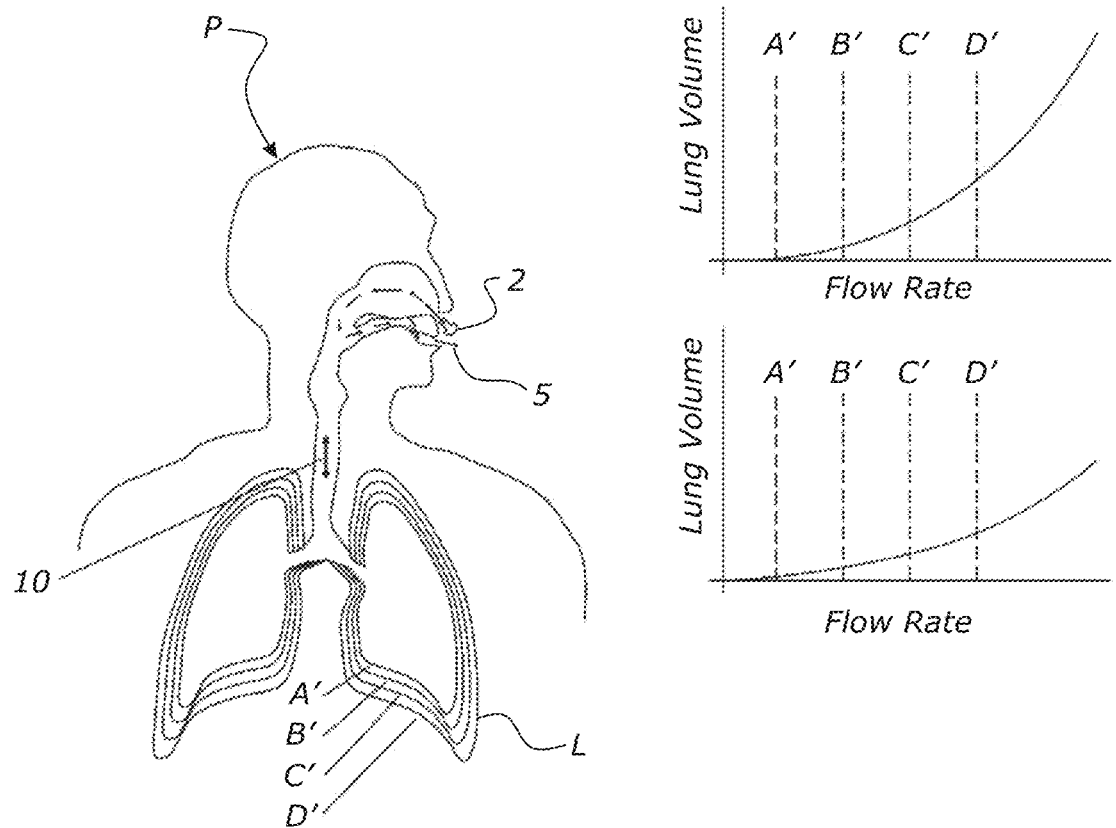
FIG. 12 shows the effects of the application of a flow rate on a patient's airway.

The relationship between an applied flow rate and the lung volume and airway pressure is shown in FIG. 12. FIG. 12 shows a patient P being provided with a flow of gases from interface 2. The graphs show that as the flow rate increases from A' to D' the lung volume also increases and a flow 10 is generated into the patient's lungs L.

As can be appreciated the application of an oscillating or otherwise varying flow rate is preferable when the patient is not spontaneously breathing as otherwise there will be no (or at least very minimal due to cardiogenic pulsing) flow from the patient's lungs. However, in cases where the patient may be spontaneously breathing both an oscillating or otherwise varying flow and a constant flow rate may be used, and the concentration of CO2 or another targeted gas used to determine airway patency.

Correlation Between Delivered Flow Rate and Targeted or Monitored Gas.

The correlation may be based on the flow rate of the gases (as a flow rate signal) with a concentration of the targeted gas. Other properties of the targeted gas could also be correlated with the flow rate signal such as flow rate.

The correlation may be based on a comparison between a waveform property of the flow of gases, and a waveform property of the monitored gas signal. A wave form property could be any feature of the wave. Some non-limiting examples of waveform properties are: frequency, amplitude, phase, shape, gradient Additionally or alternatively, the correlation could be based on a comparison between a first shape or profile of the delivered flow and a second shape or profile (or subsequent shapes of profiles) of the monitored gas signal. The first shape or profile of the delivered flow could be at least partially repeating. By way of example the first shape or profile could be a peak or trough in the delivered flow and the second shape or profile a similar or substantially identical waveform shape or profile in the monitored gas signal.

Additionally, or alternatively the correlation could be based on the comparison of one or more or: the frequency of the flow, the amplitude of the flow, the wave shape or wave form of the flow, the phase of the flow, a change over time of the flow (for example a decay or driving of said flow), with one or more of: a frequency (or range of frequencies) of the monitored gas signal, an amplitude of the monitored gas signal, an amplitude of the monitored gas signal at a particular frequency, a wave shape or wave form of the monitored gas signal, a phase of the monitored gas signal, a change over time of the monitored gas signal.

One specific method of correlation described above it the comparison of the frequency of the flow (or flow signal) with a frequency (or range of frequencies) of the monitored gas signal.

Alternatively or additionally, the correlation may be based on a comparison between one or more of: a signal edge or transition portion of the wave shape of the flow, a local maximum or minimum, or point of inflection of the wave shape of the flow, a gradient of a portion, or a gradient at a discrete point of the flow, a number of peaks and/or troughs of the flow in a given time period or a pre-determined time period with one or more of: a subsequent signal edge or transition portion of the wave shape of the monitored gas signal, optionally, when the subsequent signal edge or transition portion of the wave shape of the monitored gas signal is located within a time period after the signal edge or transition portion of the wave shape of the flow, a subsequent local maximum or minimum, or point of inflection of the wave shape of the monitored gas signal optionally, when the subsequent local maximum or minimum of the wave shape of the monitored gas signal is located within a time period after the signal edge or transition portion of the wave shape of the flow, a subsequent gradient of a portion, or gradient at a discrete point of the wave shape of the monitored gas signal, optionally, when the subsequent gradient of a portion, or gradient at a discrete point of the wave shape of the monitored gas signal is located within a time period after the gradient of a portion, or the gradient at a discrete point the wave shape of the flow, a number of peaks and/or troughs of the monitored gas signal in a given time period or a pre-determined time period.

The signal edge as described above may a rising edge or rising portion of a signal. The signal edge may additionally or alternatively, be a falling edge or falling portion of a signal.

Using the Correlation to Determine Airway Patency

A correlation indicative of an airway state being unobstructed or substantially unobstructed could be based on any one or a combination of the above correlation bases being above (or within) a set threshold or margin. Conversely, a correlation indicative of an airway state that is obstructed or substantially obstructed could be based on any of the above correlation bases being below (or not within) a set threshold or margin.

Additionally or alternatively, the strength of the correlation is proportional to the degree to which a patient's airway is patent.

Referring again to the specific correlation based on the comparison of the frequency of the flow (or flow signal) with a frequency (or range of frequencies) of the monitored gas signal. A patient's airway be determined to be unobstructed or substantially unobstructed when at least a component of a frequency (or range of frequencies) of the monitored gas signal is similar to a frequency (or range of frequencies) of the flow and when the amplitude of the flow at said frequency is above a threshold.

Figure 13A:
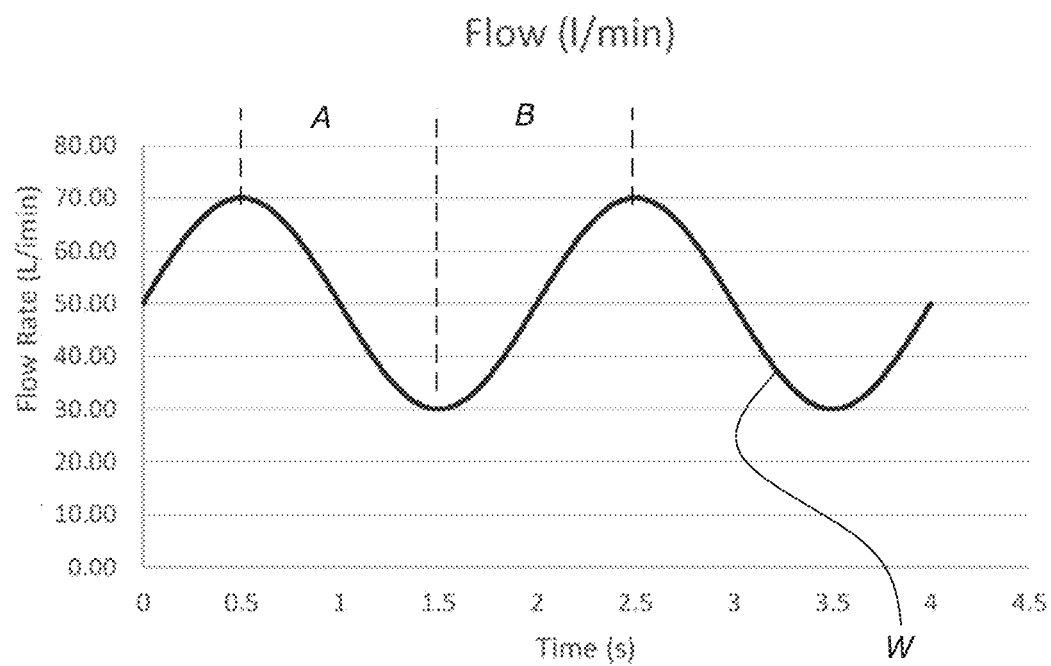
FIGS. 13A-13C show plots of an oscillating flow rate applied to a patient and the corresponding CO2 and tracheal flow measurements.
Figure 13B:
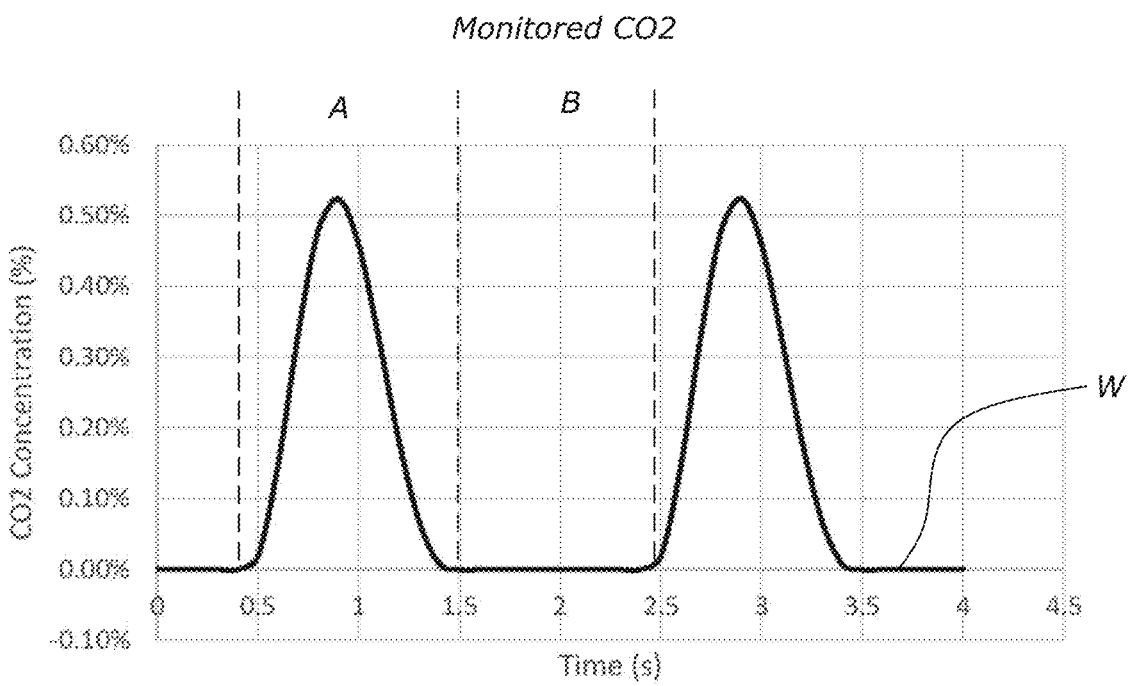
Figure 13C:
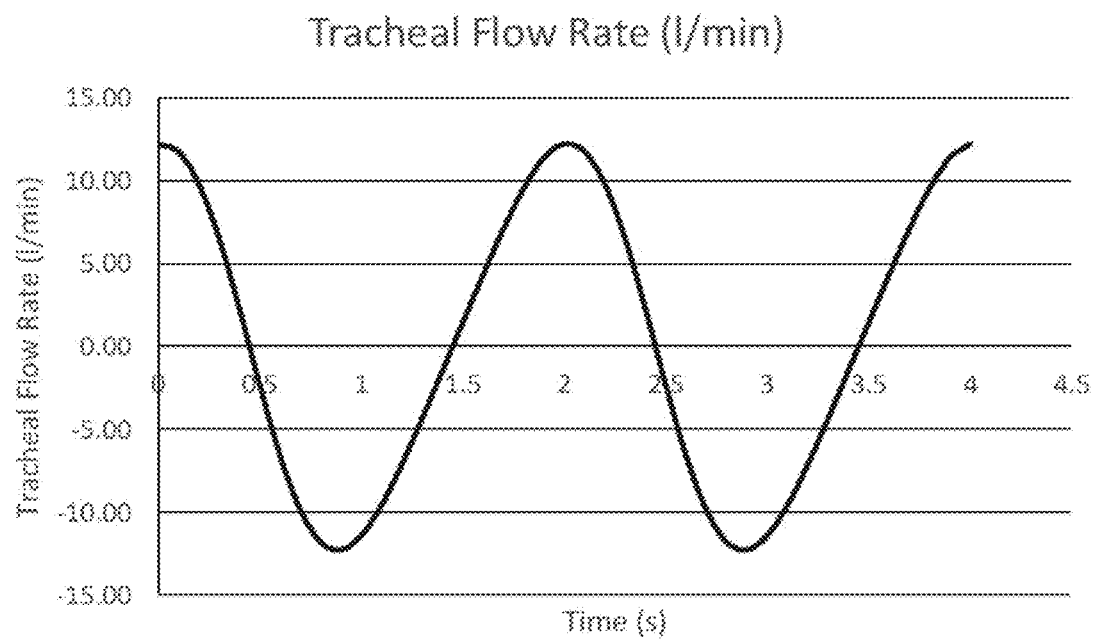
Figure 14:
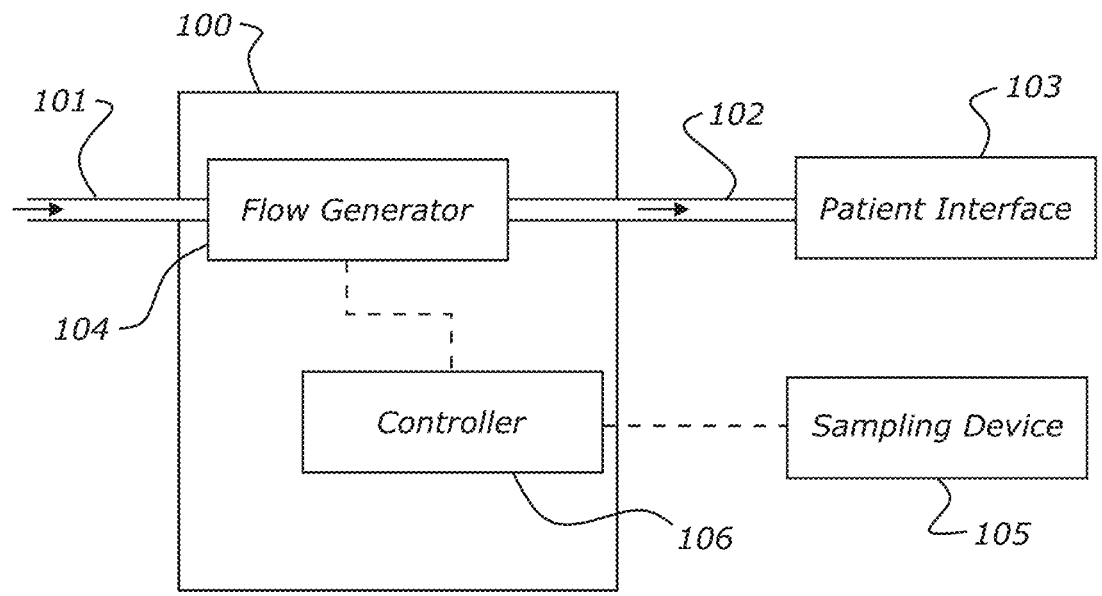
FIG. 14 shows a block diagram of an apparatus.

FIG. 13A shows a wave form W of flow rate of the delivered flow versus time. FIG. 13B shows the measured monitored gas (in this case CO2). The measured monitored gas as shown in FIG. 13A is a filtered signal to remove noise. It is observed that a decrease in flow (indicated by section A of FIG. 13A) delivered to the patient results in a corresponding peak of the monitored gas (indicated by section A of FIG. 13B). This is caused by the decrease in pressure causing a flow of gas containing CO2 from the lungs of a patient.

Further, in section B of FIG. 13A the flow rate decreases, during this section there is no flow of gases out of the patients lungs and hence no measured CO2 in section B of FIG. 13B. The frequency of the monitored gas signal W' is the same as the frequency of the delivered flow signal W. Therefore a frequency based correlation between the two would indicate a strong correlation between the monitored gas signal W' the delivered flow signal W at the frequency of the delivered flow signal (in this case the frequency of the delivered flow is around 3 hz.) The oscillating flow rate shown in FIG. 13A assists in oxygenation of the patient and helps in CO2 clearance due to flushing. More details of the oscillating flow are described above.

In some embodiments the measured monitored gas, and/or flow rate of gases as shown in FIGS. 13B and 13A respectively may be shown on a user interface described in more detail above.

Similar to the above a patient's airway is determined to be obstructed or substantially obstructed when at least a component of a frequency of the monitored gas signal is not similar or is different or is sufficiently dissimilar to the frequency of the flow and/or when the amplitude of the signal at said frequency is similar and is below a threshold.

Additionally, the monitoring of gas may be made instantaneously or in real time as a monitored gas signal. Optionally, the monitored gas signal may be sampled at periodic or regular intervals.) Additionally or alternatively, the monitored gas signal may be monitored over a set period of time for example for a procedure (such as a surgery or pre-oxygenation procedure), or a part thereof.

The airway patency determination may be based on real time measurements of the monitored gas, or measurements may be taken the monitored gas for a period of time and then subsequently analysed to derive a waveform and/or determine airway patency The correlation may be determined by one of the methods known in the art. Possible methods for determining the correlation are the Monte Carlo method, spectral analysis or Fourier transforms. In one example a Sequential Monte Carlo method can be used.

In some configurations the Sequential Monte Carlo method could be used. In the Sequential Monte Carlo method a plurality of estimates corresponding to different airway states are generated. The estimates are held in the memory of the controller and updated at each time step based on a determined model of the system. Such a model may be based on various factors of the airway or other physiological parameters of the patient. The monitored gas is then measured and compared to the updated estimate—estimates which are close to the actual measured value are given more weight than estimates which are further away. Over a plurality of time steps the estimates are re-weighted (based on the how close they are to the actual measured value). The weights of the estimates correspond to the confidence that a particular estimate is correct.

The above correlation method may be implemented by the apparatus above. The apparatus may comprise a flow generator to generate and/or provide a flow rate (optionally the flow rate may be oscillating) and deliver the flow rate to a patient; a gas sampler or (or sampling device or apparatus) configured to monitor or detect at least one targeted (or monitored gas) that is being expired or being expelled from an airway of a patient, and a controller (optionally comprising a processor) for determining a correlation between the delivered flow rate and the monitored gas and based on said correlation determining an indicator of one or more of: a determination as to airway patency, or a determination as to a location of a blockage or obstruction in the airway.

The apparatus may be configured to perform any of the methods described, or comprise any of the features described above.

Figure 5:
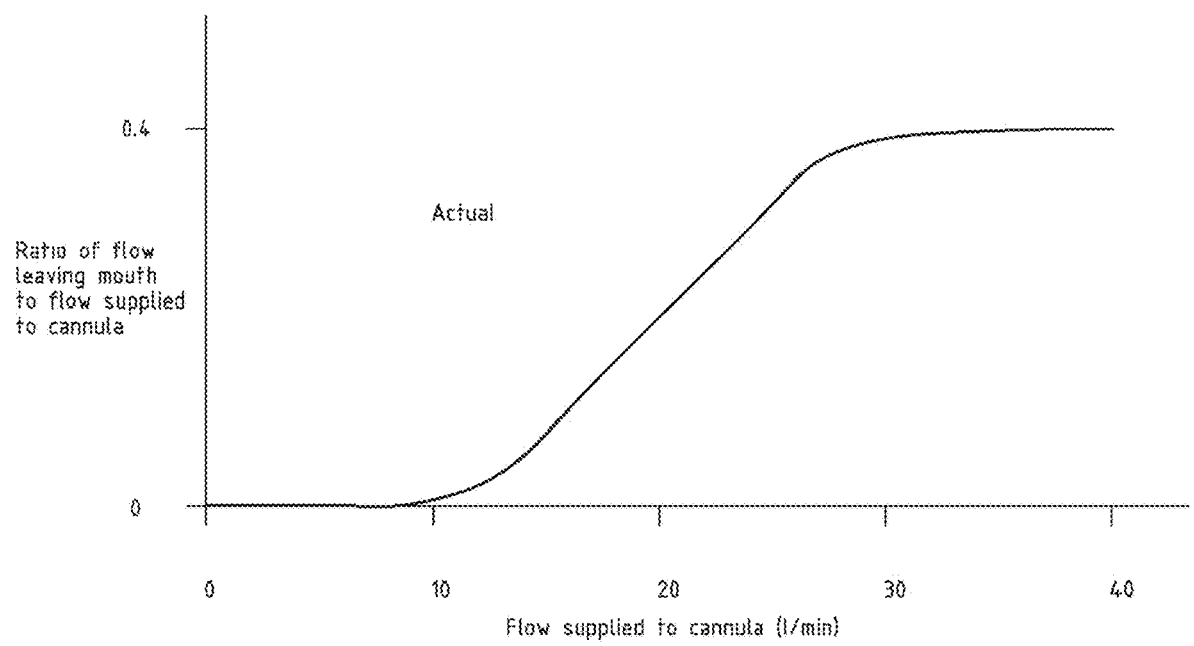
FIG. 5(A) shows an indicative ratio of gas flow leaving a patient's mouth to the flow of gas being provided or delivered to a patient interface for a patient, with FIG. 5(B) being a linear plot of 5(A) subsequently used for correction or compensation factor determination.
Figure 5:
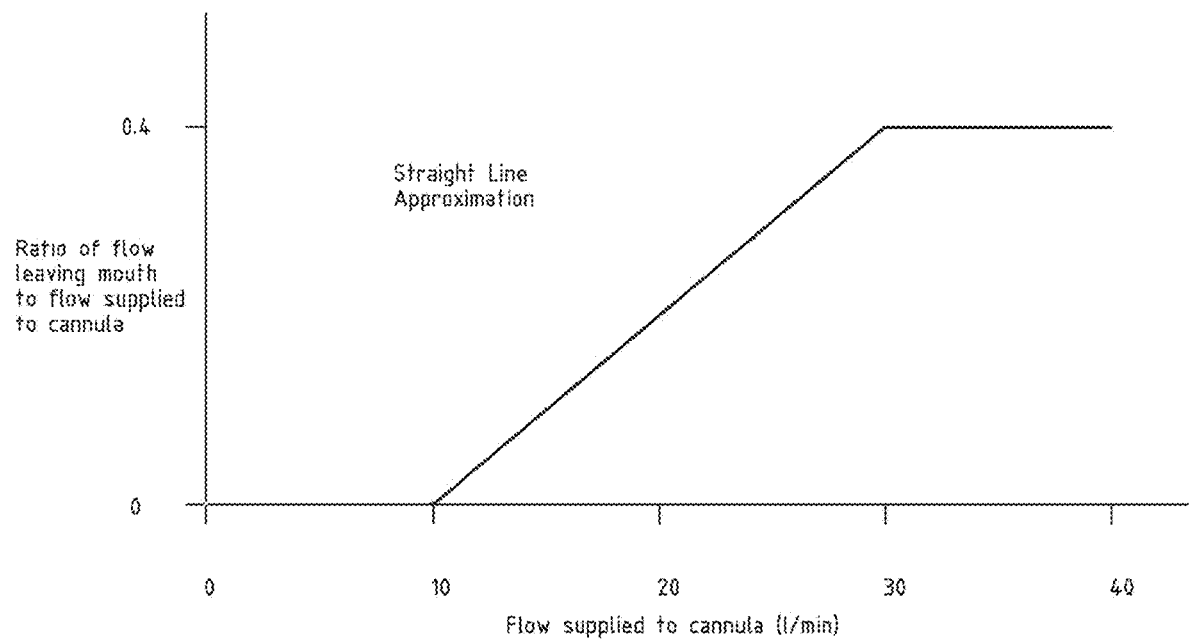

Correction for the Diluting Effect of Flow from the Nasal Cannula on Targeted Gas (e.g. CO2) Concentration Measured in the Mouth/Pharynx In order to reliably estimate the concentrations of targeted gas (e.g. CO2) leaving the mouth during cardiogenic induced expiratory pulses, it is necessary to provide for a correction or compensation to account for the dilution of the targeted gas (e.g. CO2) by the gases being provided or delivered to the patient by a flow therapy or respiratory support (e.g. a relatively high flow rate of humidified oxygen) from high flow O2 or high flow gases therapy or respiratory support leaving the mouth. This flow rate can be estimated by measuring the flow rate of gas (e.g. oxygen) entering the patient interface that is administering the flow therapy or respiratory support (e.g. a nasal cannula) and then applying a correction factor or compensation to take into account bypass leakage from the patient's nares, to then leave the flow that is exiting through the mouth. The relationship between flow entering the patient interface (e.g. nasal cannula) and flow being expired or expelled (i.e. leaving the mouth) is shown in FIG. 5. That is, FIG. 5 illustrates a ratio of mouth flow to nasal cannula flow as a function of cannula flow rate.

With reference in particular to FIG. 5 (A):

1. At relatively low gas flows, (i.e. up to about 10 l/min) a significant portion of the gas flow entering the patient interface (e.g. nasal interface, such as a nasal cannula) leaves the nose by leaking back out via the nares. Substantially little flow from the interface passes through the pharynx and out through the mouth.

2. At relatively medium flows (i.e. from about 10 l/min to about 30 l/min) an increasing fraction or proportion of the gas flow entering the patient interface leaves via the mouth, with proportionately less leaking back out of the nose via the nares.

3. Above about 30 l/min, the ratio of gas flow leaving the mouth to that entering the patient interface is substantially or almost constant. That ratio depends on the relative sizes of nares and gas delivery elements of the patient interface to the patient's airway (e.g. cannula prongs of a nasal cannula), and therefore may vary from patient to patient. An average value may be about 0.4.

In correcting for the diluting effect of the flow from the patient interface (e.g. nasal cannula) on CO2 measurements made through the mouth, it can be sufficient to approximate the curve of FIG. 5 (A) by three straight lines as shown in the FIG. 5 (B).

With respect to FIG. 5 (B), and in the first, horizontal, segment of the line from about 0-10 l/min the dilution factor may be about 1 (i.e. effectively no flow leaves the patient via the mouth and the CO2 entering the mouth by cardiogenic action is not diluted). That is:

If $F<10$ l/min: Then Dilution Factor=1

Where: F is the cannula flow rate

In the second, rising, segment of the line (from about 10 l/min to 30 l/min) the ratio of flow from the mouth to flow entering the patient interface rises linearly from about 0 to 0.4 with patient interface flow rate F. If this ratio is designated by R, the equation for the variation of R with patient interface flow rate is:

If $10$ l/min$<F<30$ l/min: Then $R=0.4(F-10)/20$

Where: R is the ratio of flow leaving the mouth to flow entering the cannula.

The dilution factor for this range of flows may then be written as:

If 10 l/min<$F$<30 l/min: Then Dilution Factor=1+ 0.4$F$($F$−10)/(20PCF)

Where: F=Patient interface (e.g. nasal Cannula) Flow Rate (l/min)

PCF=Peak Cardiogenic Flow rate (in l/min—typically 2 l/min)

Above a patient interface (e.g. nasal cannula) flow of 30 l/min, the ratio of flow from the mouth to flow entering the patient interface remains at approximately 0.4. The dilution factor for flows above 30 l/min is therefore:

If $F$>30 l/min: Then Dilution Factor=1+0.4$F$/PCF

It should be noted that the constants: 10 l/min, 30 l/min, and 0.4 are given by way of example only and are based on measurements made for an exemplified nasal cannula only. For different cannula sizes, or different patient interfaces, different empirically pre-determined constants may be used to determine the dilution factor. Dilution factors may be determined via empirical testing or modelling and programmed into the controller.

The CO2 concentration measured in the mouth/pharynx using the setup shown in FIG. 6 can be corrected for dilution by the flow from the cannula, by multiplying it by the dilution factors determined as a function of cannula flow rate as described above, to produce a corrected CO2 concentration which is used in the determinations of airway patency described below.

The step-by-step procedure for undertaking the correction is as follows:

1. The patient interface (e.g. nasal cannula) flow rate F is measured using a flow meter in the patient interface supply conduit or line. The flowmeter signal is sent to a signal processing unit.

2. The dilution factor to use in correcting the CO2 sensor signal is calculated as follows:

If $F$<10 l/min: Then Dilution Factor=1

If 10 l/min<$F$<30 l/min: Then Dilution Factor=1+ 0.4$F$($F$−10)/(20PCF)

If $F$>30 l/min: Then Dilution Factor=1+0.4$F$/PCF

Note that these sorts of dilution factors are exemplary only, and other dilution factors can be determined for other supply flow rates.

The dilution factor may be used by a controller to account for the supplied high flow therapy or flow rate of gases delivered by a respiratory support. The controller may include a flow sensor to determine the flow being supplied, and the controller may then automatically determine a dilution factor.

Where PCF is the peak flow rate induced by cardiogenesis and is typically 2 l/min, and usually in the range 1 l/min to 6 l/min. The value of PCF used in the processing unit is pre-determined from measurements on a range of typical subjects.

1. The CO2 level in the mouth/pharynx is detected as a function of time by a sensitive, high-speed CO2 sensor with sensitivity better than 0.05% and response time <0.2 sec.

2. The measured CO2 signal is multiplied by the dilution factor to give a corrected CO2 level.

3. The corrected CO2 level is displayed as a function of time on a display unit.

Figure 6:
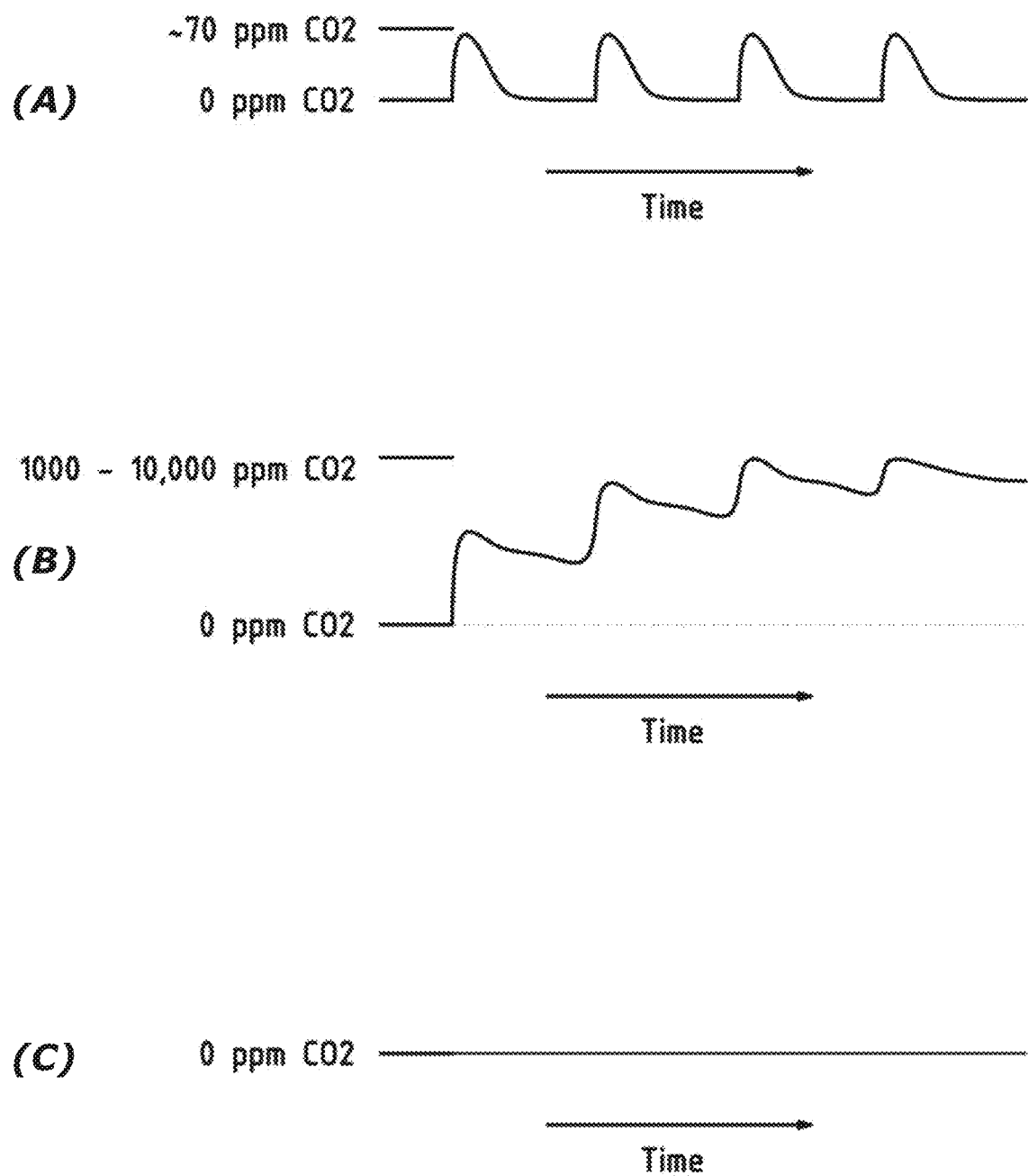
FIGS. 6(A)-(C) shows different gas concentration traces (CO2) over time depending on, (A) the soft palate being open and the trachea being open; (B) the soft palate being closed and the trachea being open; (C) the soft palate being open and the trachea being closed.

FIG. 6 shows the traces of CO2 concentration with time (before correction) that are expected from the gas sensor providing gas concentration analysis under various airway conditions. Note that the values given in FIG. 6 are indicative or approximate only, and will vary substantially from patient to patient, with the position of the sensing head of a sensor, and with the flow rate of gases (such as oxygen) supplied through the patient's nose. Rather than the absolute values, it is the qualitative features of the traces which are used to assess airway patency.

Plot (A) of FIG. 6 shows the trace to be expected in a patient where both the pharyngeal airway and the trachea are patent and CO2 is substantially cleared by apnoeic ventilation. It has the following characteristics:

The pulses in CO2 concentration occur in synchronism with the patient heartbeat or cardiogenic activity.

The baseline CO2 level is zero (or close to zero), because substantially all CO2 pumped to the pharynx on the expiratory part of the cardiogenic cycle is flushed out of the mouth by the relatively high flow of gases (e.g. oxygen) being delivered or provided to the patient (e.g. via the nose) with the flow therapy or respiratory support provided to the patient.

The baseline CO2 level does not increase with time.

Note that the peak value of the pulses in CO2 concentration may vary with time depending on variations in CO2 production by the patient (most likely as a result of variations in metabolism caused by the surgical procedure). The peak value of the pulses in CO2 concentration and their duration will also vary with the flow rate of oxygen supplied to the patient via the nose. A higher flow rate will give a lower peak value and shorter pulses.

Plot (B) of FIG. 6 shows the trace to be expected in a patient where the trachea is patent but the pharyngeal airway from the nose is blocked. This could be caused—for example—by the soft palate falling down and blocking the airway. In this case, no flushing flow reaches the mouth/oropharynx and the trace has the following characteristics:

In the early stages of a blockage, pulses in CO2 concentration will be seen because CO2 is still produced by the lungs and pumped up to the mouth/oropharynx by cardiogenic action. The pulses are synchronized to the patient's heartbeat.

Gas arriving at the oropharynx or mouth from the trachea is not cleared through the mouth by flushing flow. The only mechanisms available to clear it are diffusion, auxiliary air movements outside the mouth causing residual flow/turbulence inside it, and patient movement. In general, these clearance mechanisms will not be sufficient to substantially clear all CO2 from the oropharynx, and so the baseline level of CO2 rises with time. Note that the rate of rise may vary depending on the patient's metabolic rate, the resistance of the trachea to cardiogenically induced flow, and the level of residual flushing from external air movement or patient movement.

The CO2 concentration in the oropharynx or mouth will rise as it fills with gas pumped from the lungs by cardiogenic action. It may eventually approach the CO2 concentration in the lungs themselves. In the absence of residual clearance by external air movement of patient movement, the amplitude of the pulses in concentration will therefore be expected to fall as the baseline concentration of CO2 in the pharynx approaches that in the lungs. Note that even when the baseline concentration of CO2 in the oropharynx reaches that in the lungs, the baseline level will still be expected to rise slowly with time as the partial pressure of CO2 builds up in the blood due to ongoing metabolic action (and therefore its concentration in the lungs increases over time).

It should be noted that only a small flow from the nose is necessary to fully clear CO2 from the oropharynx, and so this trace would not be expected for a partial blockage of the pharyngeal airway which still allowed flows greater than 1-5 l/min from the nose into the mouth. Under these circumstances, measurement of splinting pressure in the airway is necessary, and this forms part of a separate claim.

Plot (C) of FIG. 6 shows the trace expected in a patient where the trachea is blocked and the pharyngeal airway is open. No CO2 is pumped to the oropharynx by cardiogenic action but flushing with oxygen occurs. The trace remains substantially at zero or a baseline concentration.

In conventional ventilation practice, clinicians monitor capnograph traces by eye to gain comfort that CO2 is being cleared from the patient. In the present application, it is possible to implement a gas sensor with a suitable controller which allows for the recognition of the characteristics of the traces described above and sounds or generates a warning or an alarm if conditions (B) or (C) are detected.

The description below is one example of such software processing to distinguish between conditions (A) and (B), and (A) and (C).

To distinguish between signals (A) and (B) it should be noted that with both the soft palate and the trachea open, signal (A) consists of a regular series of pulses in CO2 concentration, synchronised with the heartbeat of the patient. In between each pulse, the concentration of CO2 in the mouth/pharynx falls to zero because the pharynx is flushed with a high flow of pure oxygen from the nasal cannula. However, if the soft palate is closed, the CO2 level in the mouth/pharynx rises to greater than 1000 ppm. A level of CO2 which is continuously greater than 1000 ppm for a time period of several heartbeats therefore indicates a problem with the soft palate.

It will be appreciated that the following routines or procedures may be implement or executed by a programmable device or devices based on a computer readable instructions, software logic or hardware logic. Suitable programmable devices may include, but not be limited to, micro-controller, micro-processor, CPU, ASIC (application specific integrated circuit), or hardware or any other programmable hardware device, system or platform. It will also be appreciated that the routines and procedures described can be implemented by the controller of the flow rate delivered for a high flow therapy or flow rate for a respiratory support.

An example of a process or routine or procedure (e.g. may be implemented via software) to determine condition (B) may be as follows:

1. The signal processing unit continuously monitors the gas concentration level (e.g. a CO2 concentration level) from the sensor.

2. If the gas concentration level rises above a threshold value (e.g. 1500 ppm) (this is a typical value, but other range of values used may be from about 100 ppm to about 4000 ppm when for example 100% pure oxygen is supplied to the patient interface) a software flag is set and a counter started. The counter counts heartbeat pulses from a plesythmograph sensor (Oxygen saturation sensor) attached to the patient. Alternatively, the counter can also be arranged to count heartbeats in the signal from an ECG attached to the patient.

3. The flag is reset. This flag or counter can be implemented as a software flag or counter. The counter is stopped and zeroed if the gas concentration (e.g. CO2 concentration) level subsequently falls below the threshold value (e.g. the 1500 ppm referred to above).

4. Each time the counter is incremented, its value is checked. If the value exceeds a set threshold (a typical value set would be 30, but it may be in the range 10 to 120) an alarm or warning or other indicator can be generated or sounded to indicate condition (B) (i.e. soft palate closed, trachea open).

The same routine may be used or implemented to detect closure or obstruction or blockage of the soft palate when injection of a targeted gas such as a benign tracer type gas or other targeted gas is used. In such situations, the concentration of targeted gas (such as a benign medical or otherwise tracer gas) for which the software flag is set would be, for example, 10% of the initial concentration of targeted gas (e.g. a benign medical tracer gas) that is provided to the patient)

An example of a process or routine or procedure (e.g. via software) to determine condition (C) may be as follows:

1. The signal processing unit continuously monitors the targeted gas concentration (e.g. CO2) level from the sensor.

2. A counter is provided e.g. a software counter, which is zeroed at the start of the procedure, or if a reset button is pressed or activated by the clinician.

3. Each time the targeted gas concentration (e.g. CO2) level rises above an upper threshold value (e.g. 250 ppm) and then falls below a lower threshold value (e.g. 200 ppm), the software counter is decremented.

4. At the same time, pulses from a plesythmograph sensor (Oxygen saturation sensor) are fed to the signal processing unit.

5. Each time a plesythmograph pulse occurs, the software counter is incremented and its value monitored.

6. If the value of the software counter exceeds a certain threshold (a typical value set would be about 30, but it may be in the range of about 10 to 120) an alarm or warning or other indication can sounded or provided to indicate condition (C) (trachea closed).

The same software routine or algorithm can be used to detect closure of the trachea when injection of a targeted gas such as a benign tracer type gas or other targeted gas is used. In such situations, the pulse of targeted gas tracer gas would be detected by setting a threshold of 1% of the tracer gas concentration injected into the patient (for the rising part of the tracer cardiogenic pulse), and 0.75% of the tracer gas concentration injected into the patient (for the falling part of the tracer cardiogenic pulse).

It should be noted that the counter used to determine condition (B) is a different counter to that used to determine condition (C).

Monitoring Clearance of Tracer Gas for Assessing Airway Patency

Figure 7:
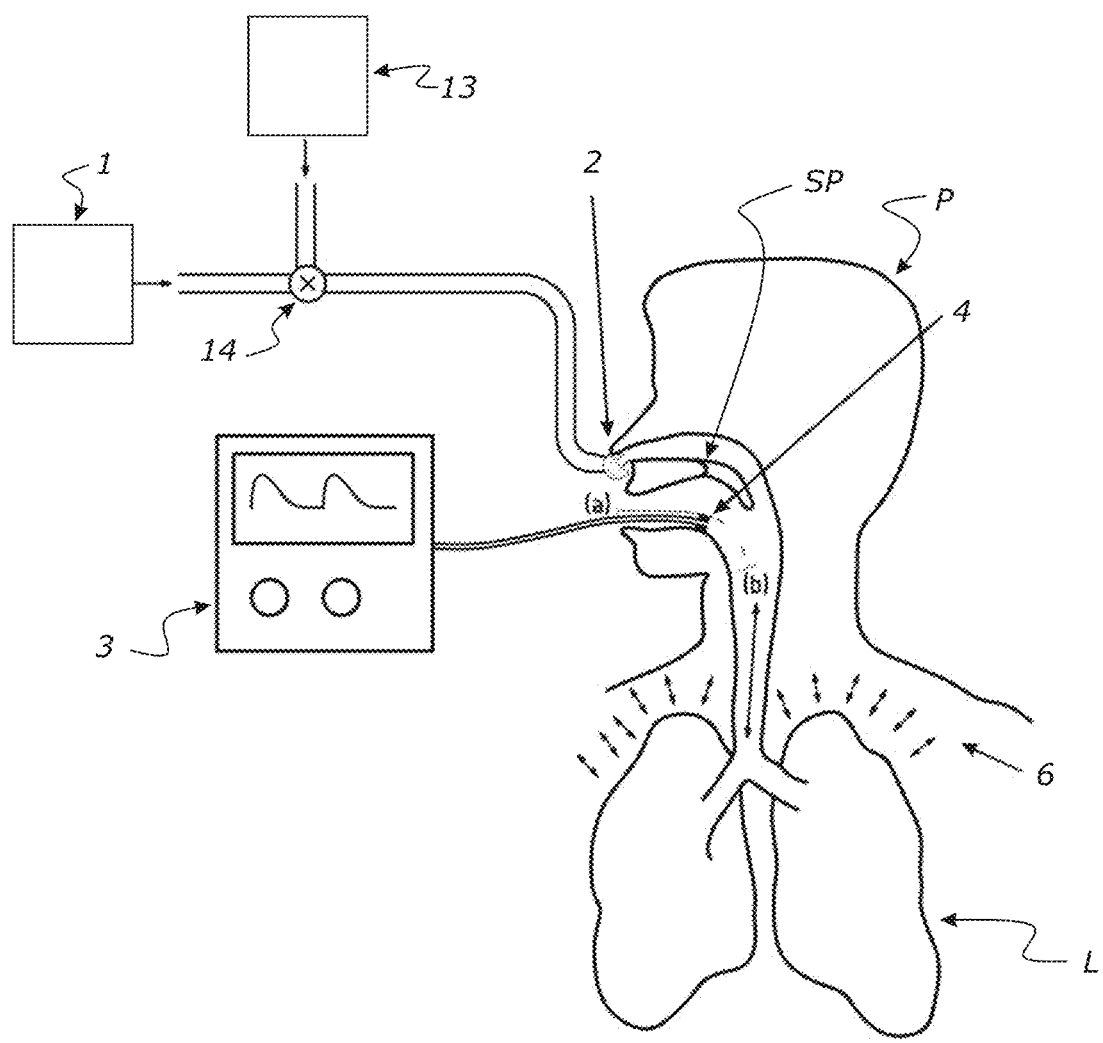
FIG. 7 shows a further configuration of a system implementing a method as disclosed herein in which a sensor in the form of a gas analysing sensor is provided inside the patient's mouth or oral cavity and a targeted gas is provided via a second source of gas.

FIG. 7 shows an example of a system for assessing airway patency by monitoring clearance of a targeted gas (e.g. a benign tracer gas) being expired or expelled from the lungs by cardiogenic action.

The anaesthetized and paralyzed patient P is apnoeically ventilated using a relatively high flow of gas (e.g. humidified oxygen) supplied via a patient interface (e.g. nasal cannula 2). The flow rate provided or delivered to the patient via such a flow therapy or respiratory support is high enough to achieve at least some or the necessary splinting pressures to mitigate against atelectasis and help ensure sufficient absorptive capacity of oxygen by the lungs to avoid desaturation.

The gas flow rate may be delivered at a constant flow rate. Alternatively, the flow therapy or respiratory support may be delivered with an oscillating (positive) flow rate to the patient or superimposed oscillations may be delivered. Optionally, an oscillations flow is delivered to accentuate the expiration of CO2 or tracer gases.

Where a high flow gas is delivered by a high flow therapy or respiratory support method or apparatus to a patient, such a flow rate can be generated to comprise various components with one or more parameters (e.g. flow rate) that can be adjusted, including being adjusted to oscillate. Each parameter might be adjusted independently, or in dependence on other parameters. This provides a varying gas flow (varying gas flow parameters). The varying gas flow (with oscillations) assists with gas removal (e.g. expired or expelled CO2 or other gases, including for example targeted gas or benign tracer gas removal) and can assist with oxygenation or the provision or delivery of other gases (e.g. targeted gas or benign tracer gas) to a patient's airway or respiratory system. As an example, the gas flow could comprise a base flow rate component that does not vary, combined with one or more oscillating flow rate components, each at different frequencies. This generates an overall gas flow waveform that varies. The flow therapy apparatus can be controlled through valves, blower controller and/or other modulating devices to generate the flow rate components. PCT application PCT/IB2016/051820 describes the use of oscillating components and is incorporated herein in its entirety.

The supply system to the patient interface incorporates a proportional or selector valve 14 which enables the flow to the patient interface to be controlled and optionally switched from a first gas source 1 (such as an oxygenated gas source) to source 13 of gas including a targeted gas (e.g. a mixture of oxygen and a benign tracer gas). In this example, a 50:50 mix of nitrogen/oxygen is used, but the relative concentrations of oxygen and tracer gas may be varied and a different tracer gas may be used provided that it does not compromise the patient or operating room procedure.

The proportional or selector valve 13 can be configured so that it switches the flow from one source to the other without interrupting the net flow to the patient interface (e.g. nasal cannula 2), and in this manner without causing reduction of the splinting pressure in the airway resulting from the flow delivered via the patient interface.

The flow of nitrogen/oxygen mix may be controlled independently by a second valve between zero and a maximum rate limited by the risk of barotrauma to the patient. As mentioned previously herein, precautions to avoid barotrauma (for example a pop-off valve to release pressure in the nasal cannula) can be implemented. These are not shown in the figures.

The patient's mouth is open so that flushing flow entering via the nose can travel through the pharynx and exit via the mouth.

A sensor such as a gas sensing head 4 can be placed in the mouth/oropharyngeal region of the patient. The gas sensing head may part of, or be attached to a gas sensor (not shown). There is considerable latitude in the positioning of the head which should be placed along the base of the mouth/oropharynx anywhere between the positions (a) and (b) as shown in the diagram. Position (a) is at the base of the mouth entrance, between the teeth and position (b) is at the entrance to the trachea. Note that the sensor head should not be placed in the valleculae as this risks blocking gas flow into the sensor and is also not directly in the gas stream coming from the trachea. The range of sensing head provides the clinician with flexibility to avoid obstructing the surgery site depending on the procedure to be carried out. The sensor may be part of a sampling device or apparatus as described above.

The sensing head is connected to a sensitive side stream nitrogen sensor which aspirates a sample of gas from the mouth/oropharyngeal region at low flow. The flow rate aspirated into the sensor should generally be less than 200 ml/minute (one fifth of the peak anticipated cardiogenically-induced flow in the trachea). If necessary, standard precautions should be taken to avoid aspiration of fluids and water vapour into the sensor head, such as using a water trap or a filter in conjunction with semi-permeable tubing of a material such as NAFION. These are not shown in the figures.

The clinician assesses airway patency by executing a measurement procedure as follows:

1. The patient is first fully oxygenated (saturation greater than 98%) using either high nasal flow of humidified oxygen of at least 70 l/min, and 1 cmH2O pharyngeal splinting pressure or bag and mask ventilation (or a combination of these).

2. The humidified oxygen supply via the nasal cannula is then removed for 1 or 2 seconds. This removes the splinting pressure and allows the lungs to deflate slightly.

3. A humidified nitrogen/oxygen mix at high flow (70 l/min or greater), is then applied for several seconds. This partially reinflates the lungs, but now with nitrogen/oxygen mix, thereby ensuring that the mix reaches the lungs.

4. The humidified oxygen supply is restored without allowing the lungs to deflate 5. The variation of concentration of nitrogen in the mouth/pharynx is monitored with time as it is pumped out of the lungs by cardiogenic action and swept out of the mouth by the high oxygen flow.

Figure 11:
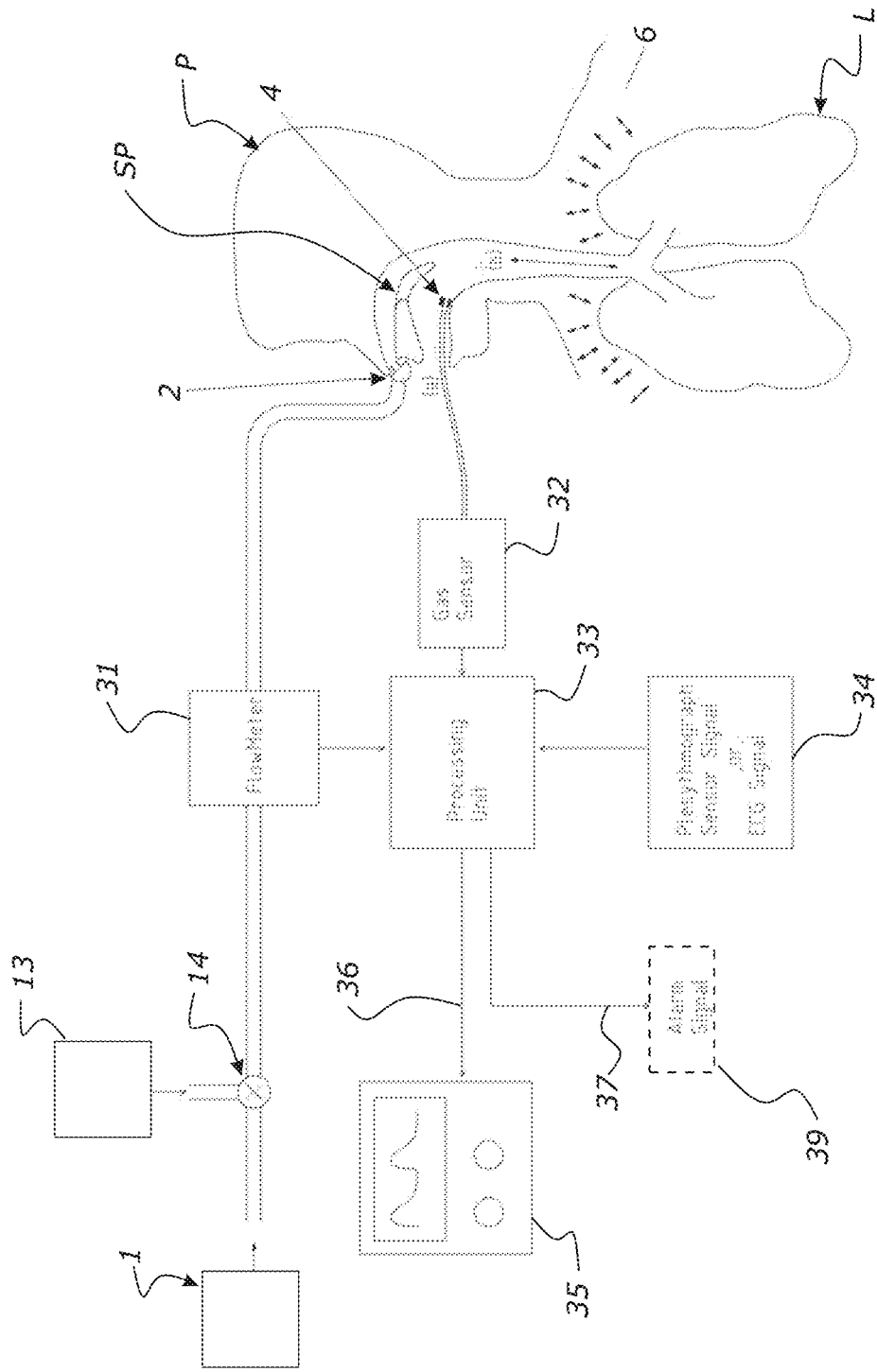
FIG. 11 shows a further configuration of a system implementing a method as disclosed herein in which a sensor in the form of a gas analysing sensor is provided inside the patient's mouth or oral cavity, and processing unit or controller receives data relating to the gas concentration being expired or expelled from a patient's mouth, ECG data, a flow rate of the flow therapy or respiratory support being provided to the patient, and the ability for warnings or alarms to be indicated resulting from processing of such data/measurements.

FIG. 11 discloses a further configuration, similar to the configuration as disclosed in FIG. 7, comprising a correction or compensation system. The system comprises a processing unit 33, the processing unit has at least one data input to read data from various other components of the system, and at least one data output to send data to various other components.

A flowmeter 31 is disposed in a gas delivery conduit, between the gas sources (1, 13) and the nasal cannula 2. The gas sources may be those as described above (for example a first gas source 1 (such as an oxygenated gas source), and a source 13 of gas including a targeted gas (e.g. a mixture of oxygen and a benign tracer gas.) The flow meter measures the flow rate of the gases provided by the gas sources (1, 13) through valve 14. The flow meter may measure mass flow gate, or volume flow rate or any other signal proportional to the flow rate of gases to the nasal cannula 2. The data from the flow meter is provided to the processing unit 23

A gas sensor 32 is provided to gas sensing head 4, the sensing head may be similar to that described in relation to FIG. 7. The output of the gas sensor 32, and gas sensing head 4 are provided to the processing unit 23.

Also provided is to the processing unit is a signal indicative of a patient parameter from a plesythomograph sensor, or an Electrocardiograph (ECG). The patient parameter may be.

The processing unit, using the aforementioned inputs may calculate or apply a correction or compensation factor. The compensation factor, as described previously, may compensate for the dilution of gases caused by the provision of flow therapy or a respiratory support provided or delivered to the patient P (for example from flow sources 1, 13 and via a patient interface, such as a nasal interface). The flow therapy may dilute a targeted gas, or dilute other gases which may be measured (for example $CO_2$). The processing unit may also determine or estimate airway patency, for example the processing unit may analyse information from associated components (for example gas sensor 32, flow meter 31, and ECG 34) to determine airway patency, and for example any of the conditions (A), (B), and (C) as described above.

A display 35 is provided to display at least a data output 36 from the processing unit 33. The data output 36 may be related to any of the conditions (A), (B), and (C) as previously described and/or may be the raw data measured from any of the components attached or connected to the processing unit. In some embodiments the display acts to display the concentration or partial pressure of $CO_2$ over time, as measured by gas sensor 32, and/or gas sensing head 4. The display 35 may allow a clinician to directly monitor variables or measurements of the system.

The processing unit may take input from at least one or more or even all the components as described above to provide an alarm output 37. The alarm output may comprise one or more alarm signals 39. The alarm signal(s) 39 may relate to the conditions (A), (B), and (C), or other various states of airway patency. The alarms may be audibly or visually, or otherwise indicated to a clinician.

Figure 8:
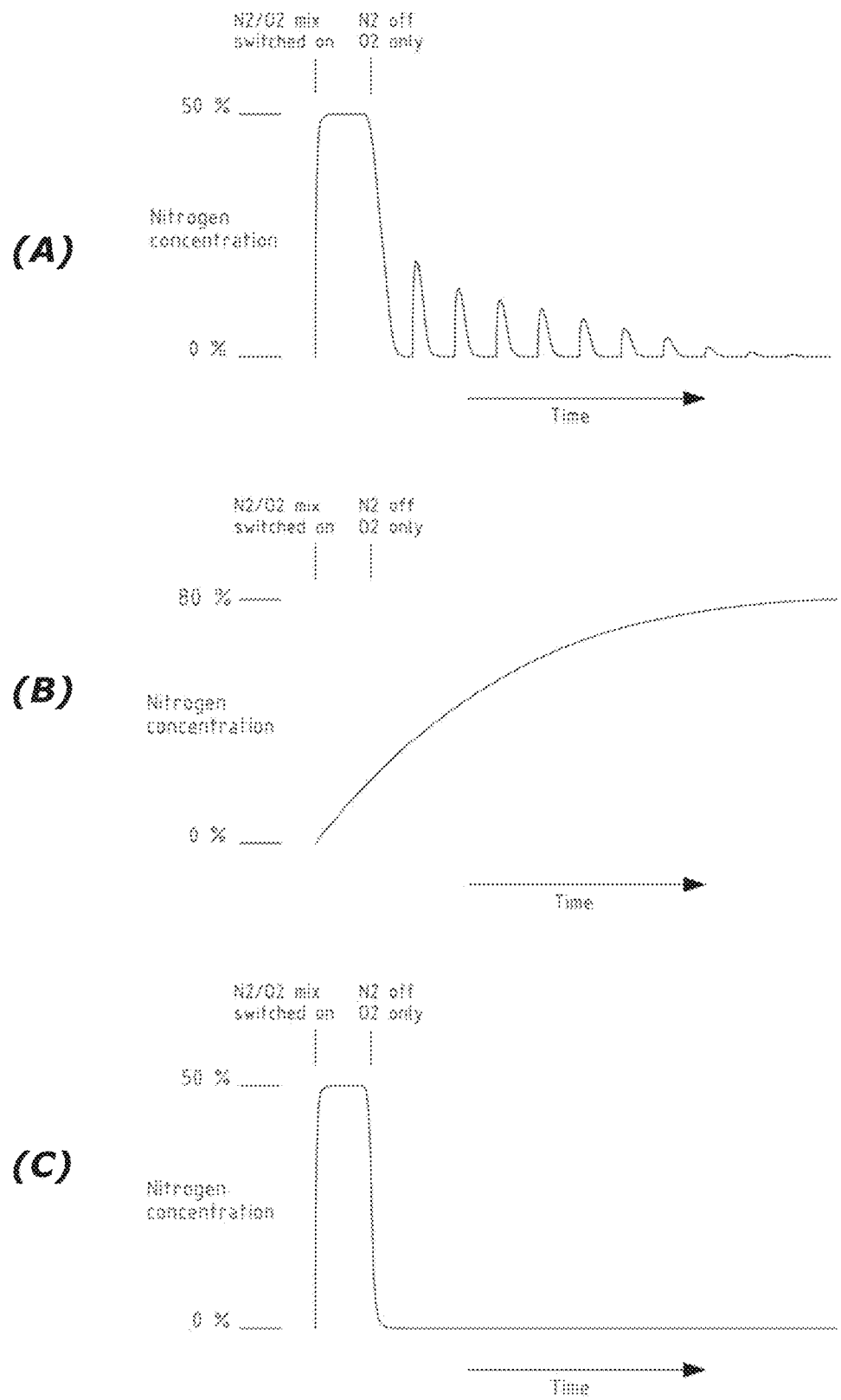
FIGS. 8(A)-(C) show shows different gas concentration traces (N2) over time depending on, (A) the soft palate being open and the trachea being open; (B) the soft palate being closed and the trachea being open; (C) the soft palate being open and the trachea being closed, when the configuration of FIG. 7 is implemented.

FIG. 8 shows the traces of nitrogen concentration with time that are expected from the sensor under various airway conditions. Note that the values given in the diagram are approximate only, and will vary substantially from patient to patient, with the position of the sensing head, and with the flow rate of oxygen supplied through the nose. Rather than the absolute values, it is the qualitative features of the traces which are used to assess airway patency.

Plot (A) of FIG. 8 shows the trace expected when both the pharyngeal airway and the trachea are patent. While the 50:50 nitrogen/oxygen mix is applied to the patient interface (such as a nasal cannula), the concentration of nitrogen goes up to 50%. When the flow is switched back to oxygen only, any nitrogen remaining in the pharynx is immediately flushed out through the mouth. Following that, nitrogen is pumped up to the pharynx from the lungs in pulses by cardiogenic action. Oxygen is also drawn into the lungs, diluting the nitrogen remaining there and so the amplitude of the pulses in concentration of the nitrogen decreases with time, eventually becoming zero when all nitrogen is pumped out of the lungs.

Note that the magnitude of the pulses is exaggerated in the diagram for illustrative purposes. Nitrogen coming from then lungs will be substantially diluted when the flow is switched back to oxygen only, and peak concentrations of approximately 0.57-3.4% would be expected in the first pulse if a 50:50 nitrogen/oxygen mixture were used.

The pulses in concentration of nitrogen are synchronized with the patient's heart beat or cardiogenic activity.

Plot (B) of FIG. 8 shows the trace expected when the pharyngeal airway is blocked, but the trachea is open. In this case no nitrogen from the patient interface (e.g. nasal cannula) passes into the oropharynx, and there is no flushing flow. Instead, as soon as oxygenation is stopped air enters the oropharynx via the open mouth by a combination of diffusion and low speed flow induced by the gas sensing head. The nitrogen concentration rises to that of air (80%).

Plot (C) of FIG. 8 shows the trace of concentration as it varies over time expected if the trachea is blocked but the pharyngeal airway is open. When the 50:50 nitrogen/oxygen mix is introduced via that cannula, the concentration of nitrogen in the oropharynx immediately rises to 50%. When the flow is switched back to oxygen only, the oropharynx is immediately flushed and the nitrogen concentration drops to zero. Because the trachea is blocked, no nitrogen may be introduced into the lungs and there no nitrogen may be pumped up the trachea by cardiogenic action. No periodic variation in the concentration of nitrogen may be observed after the flow is switched back to oxygen only.

If the pharyngeal airway is partially blocked, and the trachea is open, then a small amount of nitrogen may reach the lungs when the 50:50 nitrogen/oxygen mix is applied via the nasal cannula. In this case, a few small residual pulses in nitrogen concentration may be observed after the flow is switched to oxygen only, together with a longer oropharyngeal flushing time. This condition can be checked to eliminate the possibility of misinterpretation of the traces by monitoring the airway pressure—which is the subject of a separate claim.

The algorithms for determining the 'fault' conditions (B) and (C) above in relation to FIG. 8 are described above in relation to the monitoring of CO2 to determine airway patency. When a targeted gas such as a benign tracer gas is used, it is certain concentration thresholds of that tracer gas that are used to trigger the software counters rather than thresholds of CO2. Also note that the thresholds are different for tracer gas than they are for CO2 due to the initial concentration of tracer gas in the lungs being much higher than the concentration of CO2. The algorithms may be stored as computer readable and executable instructions in a memory device associated with a controller (as described above). The controller being configured to read and execute the algorithms to cause the electronic controller to determine airway patency based on processing targeted gas measurements.

All thresholds are given an examples only and are indicative of the method or system to be implemented.

Monitoring airway pressure to ensure sufficient flow for splinting and mitigation of atelectasis The high flow of gas (e.g. of oxygen) provided or delivered via the nose creates a small splinting pressure in the airway (typically 0.5-5 cmH2O). Although small, this pressure helps inflate alveoli thereby mitigating against atelectasis. This may be particularly important in obese patients.

If the pharyngeal airway from the nose is partially blocked, the splinting pressure may be substantially reduced. Monitoring the pressure in the patient airway therefore provides the clinician with a means of confirming pharyngeal airway blockage that may be suspected from CO2 or tracer gas measurements as described above.

Figure 9:
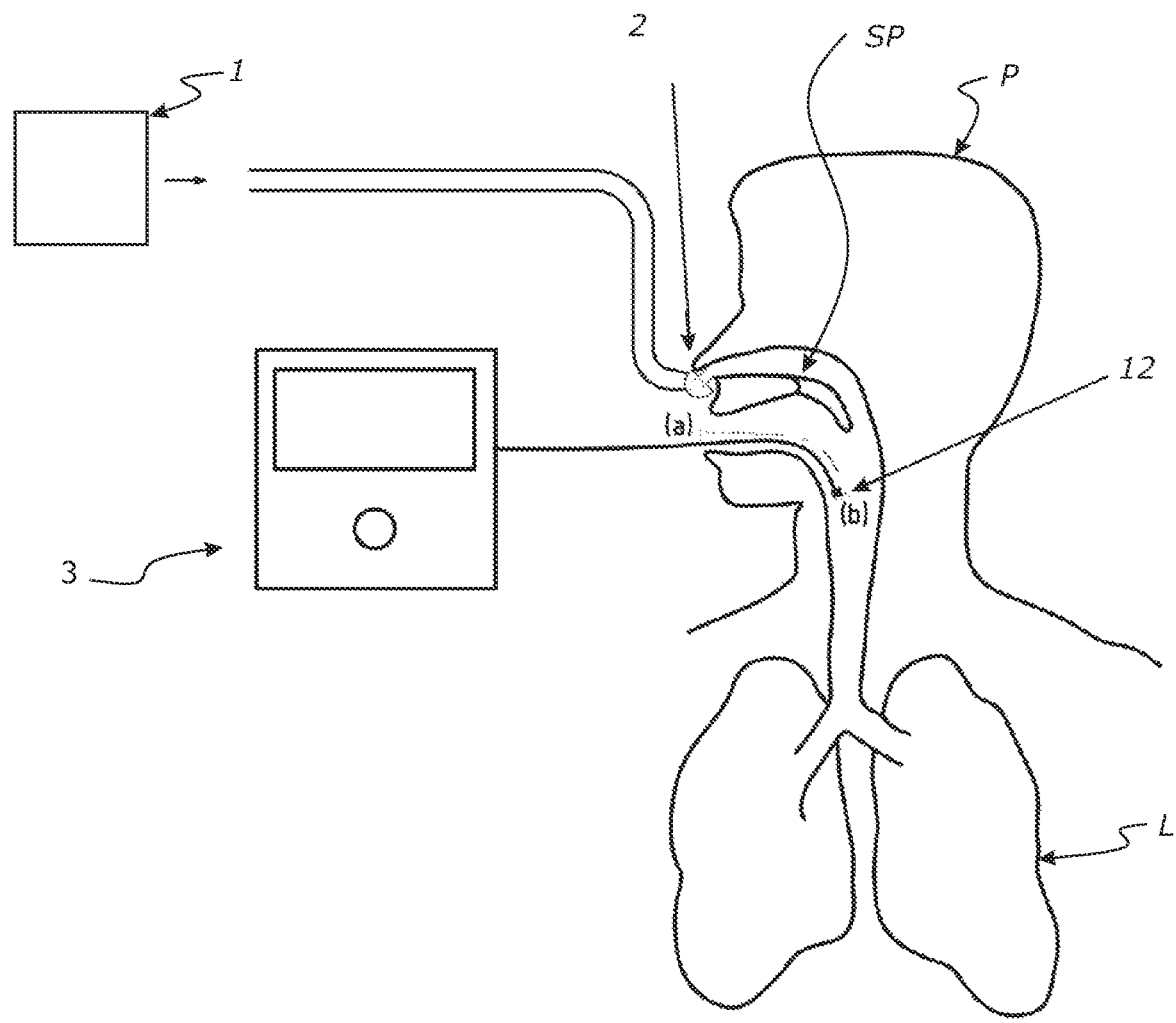
FIG. 9 shows a further configuration of a system implementing a method as disclosed herein in which a sensor in the form of a gas pressure sensor is provided inside the patient's mouth or oral cavity.

A system for measuring airway pressure to enable this confirmation is shown in FIG. 9.

A pressure transducer 12 is introduced into the apnoeic patient P airway to measure the pressure at a point just above the larynx, but out of the main flow of gases from the patient interface 2 that are exiting the mouth. It should be deeper in the airway than the sensor of the gas sensing head described above. This may be necessary to minimise disturbance of the pressure measurement due to dynamic effects from the high flow. The pressure transducer 12 may have a range from about −10 to +10 cmH2O with a sensitivity of 0.2 cmH2O or better. The transducer may have a response time of better than 0.1 second.

The patient mouth must be open for this measurement. A closed mouth may give a false indication that the pharyngeal airway is open when it is in fact partially closed.

The nasal patient interface (such as a nasal cannula 2) fitted to the nose should be the correct size for the patient nares. A cannula which is too large may give a false indication that the pharyngeal airway is open when it is in fact partially closed. A cannula which is too small may give a false indication that the pharyngeal airway is partially blocked when it is in fact open to a normal extent for the patient.

Figure 10:
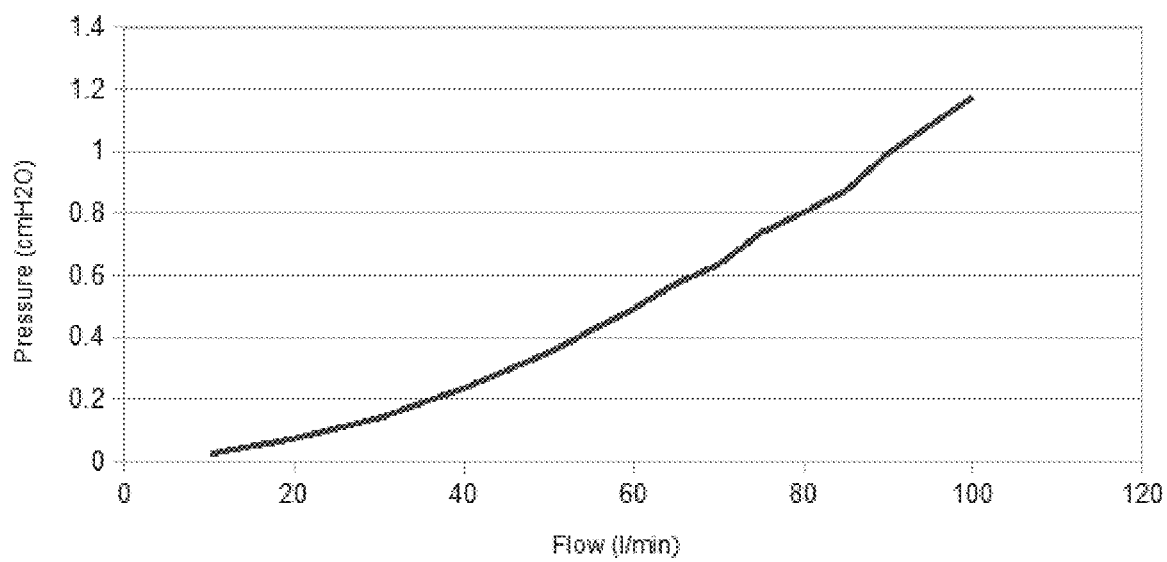
FIG. 10 is a plot of how the pressure in the airway will vary approximately with the square of the cannula flow.

If the pharyngeal airway is normally open, the pressure in the airway will vary approximately with the square of the cannula flow. For normal adults, the pressure at a cannula flow rate of 70 l/min may be in the range of about 0.5-2 cmH2O (see for example FIG. 10). A pressure of lower than 0.5 cmH2O indicates that the pharyngeal airway is partially blocked, and that the splinting pressure is likely to be substantially lower than that required for mitigation of atelectasis. A low airway pressure is of particular concern for patients who are obese, for example with body mass index (BMI) of 30 or greater.

Further confirmation of low flow from the patient interface (such as a nasal cannula) via the pharyngeal airway may be obtained by measuring turbulent pressure fluctuations at the sensor occurring with time scales of 0.1-0.5 seconds. Pressure fluctuations of 0.2 cmH2O or greater are indicative of flows of 60 l/min or higher. Under normal conditions, pressure fluctuations of less than this indicate that the flow into the pharynx is less than optimal for splinting the airway and alveoli.

The system may also comprise a display 3, and flow sources 1, 13 and a valve 14 (all of which are described in relation to FIGS. 7 and 11 above.)

It is envisaged that the system as shown in FIG. 9 can be combined with the system of FIGS. 7 and/or 11.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "(s)" following a noun means the plural and/or singular form of that noun.

As used herein the term "and/or" means "and" or "or", or where the context allows both.

Where the terminology "configured to" is used herein, that terminology could alternatively be replaced with "arranged to" or "adapted to".

Where, in the foregoing description reference has been made to integers or components having known equivalents thereof, those integers are herein incorporated as if individually set forth.

The disclosure may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the configurations describe above may be combined with each other and/or a respiratory support system or humidifier may comprise one or more of the above described configurations. Moreover, not all of the features, aspects and advantages are necessarily required to practice the present disclosure. Accordingly, the scope of the present disclosure is intended to be defined only by the claims that follow.

The invention claimed is:

1. A method for providing an indication or establishment of airway patency of a patient comprising:
   monitoring of at least one targeted gas that is being expired or being expelled from an airway of the patient,
   determining a correlation between a delivered flow rate and measurements of the at least one targeted gas as a monitored gas signal,
   based on the measurements of the at least one targeted gas for a period of time providing an indicator as to: a determination as to airway patency, a determination as to a location of a blockage or obstruction in the airway, or the correlation between the delivered flow rate and the measurements of the at least one targeted gas, and
   wherein a flow of gases is provided or delivered with an oscillating flow to the patient or superimposed oscillations of a positive gas flow is delivered to the patient.

2. The method of claim 1, wherein the oscillating flow is delivered to accentuate or facilitate the expiration or expulsion of the at least one targeted gas, such that the measurements of the at least one targeted gas for the period of time vary in response to the oscillating flow when the patient's airway is unobstructed or patent.

3. The method of claim 1, wherein the correlation is based on a comparison of one or more of:
   a frequency of the flow of gases with a frequency of the monitored gas signal,
   an amplitude of the flow of gases with an amplitude of the monitored gas signal,
   a wave shape or wave form of the flow of gases with a wave shape or wave form of the monitored gas signal,
   a phase of the flow of gases with a phase of the monitored gas signal, and
   a change over time of the flow of gases with a change over time of the monitored gas signal.

4. The method of claim 3, wherein the correlation is based on a comparison between one or more of:
   a signal edge or transition portion of the wave shape or wave form of the flow of gases,
   a local maximum or minimum, or point of inflection of the wave shape or wave form of the flow of gases,
   a gradient of a portion, or a gradient at a discrete point of the flow of gases, a number of peaks or troughs of the flow of gases in the period of time, and one or more of:
- a subsequent signal edge or transition portion of the wave shape or wave form of the monitored gas signal, when the subsequent signal edge or transition portion of the wave shape or wave form of the monitored gas signal is located within a time period after the signal edge or transition portion of the wave shape of the flow of gases,
- a subsequent local maximum or minimum, or point of inflection of the wave shape or wave form of the monitored gas signal, when the subsequent local maximum or minimum of the wave shape or wave form of the monitored gas signal is located within a time period after the signal edge or transition portion of the wave shape or wave form of the flow of gases,
- a subsequent gradient of a portion, or gradient at a discrete point of the wave shape or wave form of the monitored gas signal, when the subsequent gradient of the portion, or gradient at the discrete point of the wave shape or wave form of the monitored gas signal is located within a time period after the gradient of the portion, or the gradient at the discrete point of the flow of gases,
- a number of peaks or troughs of the monitored gas signal in the period of time.

5. The method of claim 1, wherein the patient's airway is determined to be substantially unobstructed when the correlation between the delivered flow rate and the monitored gas signal is above a threshold.

6. The method of claim 1, wherein a level of patency of the patient's airway is proportional to a strength of the correlation between the delivered flow rate and the monitored gas signal.

7. The method of claim 1, wherein the patient's airway is determined to be substantially obstructed when the correlation between the delivered flow rate and the at least one targeted gas is below a threshold.

8. A method for providing an indication or establishment of airway patency of a patient comprising:
- monitoring of at least one targeted gas that is being expired or being expelled from an airway of the patient,
- based on measurements of the at least one targeted gas for a period of time, providing an indicator as to: a determination as to airway patency, or a determination as to a location of a blockage or obstruction in the airway,
- wherein a flow of gases is provided or delivered with an oscillating flow to the patient or superimposed oscillations of a positive gas flow is delivered to the patient, and
- wherein the patient's airway is determined to be substantially unobstructed when a correlation between a flow rate of the gases delivered to the patient and a gas signal of the monitored at least one targeted gas is above a threshold.

9. The method of claim 8, wherein a flow therapy or respiratory therapy of supplied gases is delivered to the patient's airways at a flow rate of between 20 LPM and 90 LPM.

10. The method of claim 9, wherein the supplied gases are heated humidified gases.

11. The method of claim 8, wherein a flow therapy or respiratory support of the flow of gas is delivered to the patient's airway via the patient interface wherein the patient interface is of a type comprising a sealing or non-sealing interface, and may further comprise a nasal mask, an oral mask, an oro-nasal mask, a full face mask, a nasal pillows mask, a nasal cannula, or some other gas conveying patient interface system.

12. The method of claim 8, wherein the measurements of the at least one targeted gas are obtained from: measurements taken adjacent or inside the mouth or oral cavity or oropharyngeal region of the patient, measurements taken adjacent the pharynx, or a pharyngeal flow of the patient, or measurements taken adjacent or inside the nose or nasal cavity of the patient.

13. The method of claim 8, wherein determination as to the location of the blockage or obstruction in the airway is the upper airway or the lower airway.

14. A method for providing an indication or establishment of airway patency of a patient comprising:
- monitoring of at least one targeted gas that is being expired or being expelled from an airway of the patient,
- based on measurements of the at least one targeted gas for a period of time, providing an indicator as to: a determination as to airway patency, or a determination as to a location of a blockage or obstruction in the airway,
- wherein a flow of gases is provided or delivered with an oscillating flow to the patient or superimposed oscillations of a positive gas flow is delivered to the patient, and
- wherein the patient's airway is determined to be substantially obstructed when a correlation between a flow rate of the gases delivered to the patient and the at least one targeted gas is below a threshold.

15. The method of claim 14 wherein a flow therapy or respiratory therapy of supplied gases is delivered to the patient's airways at a flow rate of between 20 LPM and 90 LPM.

16. The method of claim 15, wherein the supplied gases are heated humidified gases.

17. The method of claim 14, wherein a flow therapy or respiratory support of the flow of gas is delivered to the patient's airway via the patient interface wherein the patient interface is of a type comprising a sealing or non-sealing interface, and may further comprise a nasal mask, an oral mask, an oro-nasal mask, a full face mask, a nasal pillows mask, a nasal cannula, or some other gas conveying patient interface system.

18. The method of claim 14, wherein the measurements of the at least one targeted gas are obtained from: measurements taken adjacent or inside the mouth or oral cavity or oropharyngeal region of the patient, measurements taken adjacent the pharynx, or a pharyngeal flow of the patient, or measurements taken adjacent or inside the nose or nasal cavity of the patient.

19. The method of claim 14, wherein determination as to the location of the blockage or obstruction in the airway is the upper airway or the lower airway.

* * * * *